United States Patent [19]

Degen et al.

[11] Patent Number: 5,788,862
[45] Date of Patent: Aug. 4, 1998

[54] FILTRATION MEDIUM

[75] Inventors: Peter J. Degen, Huntington; Moira H. Bilich, Massapequa; Trevor A. Staff, Bronx; John Gerringer, Port Washington; Richard Frank Salinaro, Hastings on Hudson, all of N.Y.

[73] Assignee: Pall Corporation, East Hills, N.Y.

[21] Appl. No.: 527,162

[22] Filed: Sep. 12, 1995

Related U.S. Application Data

[63] Continuation-in-part of Ser. No. 882,473, May 13, 1992, Pat. No. 5,480,554.

[51] Int. Cl.[6] ................................................ B01D 61/00
[52] U.S. Cl. ............. 210/651; 210/490; 210/500.38; 210/500.41; 210/500.35; 210/500.36; 264/4; 264/49
[58] Field of Search ................................ 210/651, 490, 210/500.38, 500.36, 500.35, 500.41; 264/22, 41, 49

[56] References Cited

U.S. PATENT DOCUMENTS

| | | |
|---|---|---|
| 3,615,024 | 10/1971 | Michaels . |
| 3,691,068 | 9/1972 | Cross . |
| 3,931,123 | 1/1976 | Vacik et al. . |
| 3,939,049 | 2/1976 | Ratner et al. . |
| 3,945,900 | 3/1976 | Klinkowski . |
| 3,977,967 | 8/1976 | Trulson et al. . |
| 3,994,860 | 11/1976 | Brousse . |
| 4,026,977 | 5/1977 | Bourganel . |
| 4,033,822 | 7/1977 | Gregor . |

(List continued on next page.)

FOREIGN PATENT DOCUMENTS

| | | |
|---|---|---|
| 0 037 185 | 10/1981 | European Pat. Off. . |
| 0 139 202 | 5/1985 | European Pat. Off. . |
| 0 202 849 | 11/1986 | European Pat. Off. . |
| 0 396 258 | 11/1990 | European Pat. Off. . |
| 2 314 215 | 1/1977 | France . |
| 224665 | 7/1985 | Germany . |
| 2 020 300 | 11/1979 | United Kingdom . |
| 2 047 162 | 11/1980 | United Kingdom . |
| 2 266 851 | 11/1993 | United Kingdom . |

OTHER PUBLICATIONS

Philip A. Schweitzer, Handbook of Separation Techniques for Chemical Engineers, pp. 2-9-2-17.
Kirk-Otmer Encyclopedia of Chemical Technology (3rd Edition), vol. 23, pp. 439–440.
Merrill et al., *ASAIO J.*, 6, 60–64 (1983).

(List continued on next page.)

*Primary Examiner*—Ana Fortuna
*Attorney, Agent, or Firm*—Leydig, Voit & Mayer, Ltd.

[57] ABSTRACT

The present invention provides a filtration medium comprising an ultrafiltration membrane and a monomer surface coating thereon of an acrylic or methacrylic acid monomer having alcohol functional groups, wherein the filtration medium after having been fully dried is characterized by having a titer reduction of at least about $10^3$ with respect to PP7 bacteriophage and a critical wetting surface tension of at least about 70 mN/m. The filtration medium preferably further comprises a fibrous nonwoven web embedded in the membrane. The present invention also provides a method of filtering a fluid through the present inventive filtration medium, as well as a method of preparing such a filtration medium.

44 Claims, 13 Drawing Sheets

U.S. PATENT DOCUMENTS

| | | | |
|---|---|---|---|
| 4,035,459 | 7/1977 | Kesting et al. | 264/49 |
| 4,060,488 | 11/1977 | Hoover et al. | |
| 4,134,837 | 1/1979 | Yamashita et al. | |
| 4,177,150 | 12/1979 | Inoue et al. | |
| 4,203,847 | 5/1980 | Grandine | |
| 4,207,182 | 6/1980 | Marze | |
| 4,208,508 | 6/1980 | Hashino et al. | |
| 4,320,009 | 3/1982 | Hilton et al. | |
| 4,340,479 | 7/1982 | Pall | |
| 4,358,378 | 11/1982 | Iwama et al. | |
| 4,439,322 | 3/1984 | Sonoda et al. | |
| 4,451,424 | 5/1984 | Tweedle et al. | |
| 4,473,474 | 9/1984 | Ostreicher et al. | |
| 4,481,260 | 11/1984 | Nohmi | |
| 4,618,533 | 10/1986 | Steuck | |
| 4,672,113 | 6/1987 | Wallisch et al. | |
| 4,810,384 | 3/1989 | Fabre | |
| 4,814,082 | 3/1989 | Wrasidlo | |
| 4,816,252 | 3/1989 | Stott et al. | |
| 4,822,489 | 4/1989 | Nohmi et al. | |
| 4,857,201 | 8/1989 | Black et al. | |
| 4,871,494 | 10/1989 | Kesting et al. | |
| 4,880,441 | 11/1989 | Kesting et al. | |
| 4,902,422 | 2/1990 | Pinnau et al. | |
| 4,902,424 | 2/1990 | Wrasidlo | |
| 4,906,375 | 3/1990 | Heilmann | |
| 4,908,267 | 3/1990 | Kohn | |
| 4,954,381 | 9/1990 | Cabasso et al. | |
| 4,968,733 | 11/1990 | Müller et al. | |
| 4,976,859 | 12/1990 | Wechs | |
| 4,990,252 | 2/1991 | Tomaschke et al. | |
| 4,992,221 | 2/1991 | Malon et al. | |
| 4,992,485 | 2/1991 | Koo et al. | |
| 4,997,565 | 3/1991 | Niesen | |
| 5,017,292 | 5/1991 | DiLeo et al. | |
| 5,022,990 | 6/1991 | Doi et al. | |
| 5,069,945 | 12/1991 | Wrasidlo | |
| 5,076,935 | 12/1991 | Kraus et al. | |
| 5,212,000 | 5/1993 | Rose et al. | 428/34.7 |
| 5,433,859 | 7/1995 | Degen | 210/651 |
| 5,468,390 | 11/1995 | Crivello et al. | |
| 5,480,554 | 1/1996 | Degen et al. | 210/651 |

OTHER PUBLICATIONS

Miyano et al., *J. Appl. Polym. Sci.*, 41, 407–417 (1990).

Passlack et al., *Die Angewandte Makromolekulare Chemie*, 139(2280), 175–189 (1986).

Philips Abstract on "Novel Liquid–Porosmetric Integrity for Correlating Virus Retention" (date unknown).

Ray et al., *J. Membrane Sci.*, 23, 155–182 (1985).

Technical Bulletin, "Ultrafiltration and Microfiltration—Hollow Fiber Membranes", A/G Technology Corporation (date unknown).

Tsay et al., *J. Polym. Sci.*, Part B, 1327–1365 (1990).

Tweedle et al., *Ind. Eng. Chem. Prod. Res. Dev.*, 22, 320–326 (1983).

Capannelli et al., *Characterization of Porous Solids*, Unger et al., eds., Elsevier Science Publishers B.V., Amsterdam, 283–293 (1988).

Capannelli et al., *Journal of Membrane Science*, 15, 289–313 (1983).

Chen et al., *J. Membrane Sci.*, 48, 203–19 (1990).

Database WPI, Derwent Publications Ltd., 83–28523K/12 (JP58024305 abstract) (Feb. 14, 1983).

Database WPI, Derwent Publications Ltd., 83–773589/39 (JP58139702 abstract) (Aug. 19, 1983).

Database WPI, Derwent Publications Ltd., 84–099899 (SU1028687 abstract) (Jul. 15, 1983).

Database WPI, Derwent Publications Ltd., 86–167043/26 (JP61101204 abstract) (May 20, 1986).

Database WPI, Derwent Publications Ltd., 89–181842/25 (JP1119308 abstract) (May 11, 1989).

Database WPI, Derwent Publications Ltd., 89–215629/30 (JP1151922 abstract) (Jun. 14, 1989).

Database WPI, Derwent Publications Ltd., 90–048948/07 (JP2002862 abstract) (Jan. 8, 1990).

Database WPI, Derwent Publications Ltd., 90–069979/10 (JP2021560 abstract) (Jan. 24, 1990).

DiLeo et al., *Nature*, 351, 420–421 (1991).

Doi et al., *Desalination*, 80, 167–180 (1991).

Erbe, *Kolloindnyj Zurnel*, 277–285 (1933).

Hampl et al., *Collection Czechoslov. Chem. Commun.*, 32, 4181–4189 (1967).

Kleper, *BioPharm*, 13, (Nov./Dec. 1990).

Lafrenier et al., *Ind. Eng. Chem. Prod. Res.*, 26(11), 2385 (1987).

Anderson et al., *Science*, 252, 1412–1414 (1991).

*Kirk–Othmer Encyclopedia of Chemical Technology* (3rd ed.), vol. 23, pp. 439–461 ("Ultrafiltration") (1983).

Kesting, *J. Applied Polymer Science*, 41, 2739–52 (1990).

LATEX PARTICLE CALIBRATION CURVES
(FOR 0.02 MICRON LATEX @ 250NM)

(FOR 0.038 MICRON LATEX @ 250NM)

FILTRATION MEDIUM

CROSS-REFERENCE TO RELATED APPLICATION

This is a continuation-in-part of U.S. patent application Ser. No. 07/882,473, filed May 13, 1992, now U.S. Pat. No. 5,480,554.

TECHNICAL FIELD OF THE INVENTION

The present invention pertains to filtration media, particularly filtration media comprising ultrafiltration membranes.

BACKGROUND OF THE INVENTION

Ultrafiltration (UF) and diafiltration (DF) are pressure-driven membrane separation processes which are used to separate (by a sieving mechanism) macromolecules such as proteins from solutions containing solvents and low molecular weight (MW) solutes. UF and DF processes are similar, and the same membranes can be used for both processes. In a UF process, no additional solvent (e.g., water) is added to the solution which is being filtered while filtration is in progress, whereas, in a DF process, additional solvent is added during filtration. If a solution contains macromolecules of sufficiently great size differences, then a UF or DF process can be also used to fractionate these macromolecules.

The filtration regime which comprises the UF and DF processes lies on the spectrum of pressure driven membrane separation processes between hyperfiltration (HF), also known as reverse osmosis (RO), on its fine-pored side and microfiltration (MF) on its coarse-pored side. The UF regime covers the pore diameter range between 0.001 and 0.02 µm (10–200 Å). The UF process is also described in terms of the molecular weigh cutoff (MWCO) capabilities of its membranes. The UF process generally utilizes membranes with a MWCO between about 500 and several million daltons.

Asymmetric, integrally-skinned UF membranes are prepared by a generalized process known as phase inversion in which a multicomponent polymer solution (sol) typically consisting of three components—namely, polymer, solvent, and poreformer (nonsolvent, swelling agent, or weak solvent)—is induced to separate into two interdispersed liquid phases prior to coagulation into a solid membrane gel. To effect the separation into two interdispersed liquid phases, polymer miscibility in the solvent vehicle is lowered by solvent evaporation (dry process), exchange of solvent for nonsolvent (wet process), or lowering solution temperature (thermal process).

Two general structural varieties of asymmetric, integrally-skinned, phase inversion UF membranes are known in the art. Representative of the first is that disclosed in U.S. Pat. No. 3,615,024, which is the original and still most commonly encountered variety of UF membrane, consisting essentially of a bilayer having a thin skin exhibiting what has been termed slit-like fissures or cracks, and a thick substructure containing a high concentration of finger-like intrusions or macrovoids. The macrovoids often extend from one surface to the other, although they are sometimes buried more deeply within the matrix. Ideally, an integral skin covers the macrovoids, but, in practice, some of the skin above the macrovoids is cracked, thereby breaking the integrity of the skin and enabling the passage of large particles. These membranes are supplied wetted with a pore supporting fluid since they cannot tolerate full dryness without severe loss of filtration performance. Bacteriostats, which must be washed out of the membrane before usage, are often present in membranes that are supplied wet. Some manufacturers indicate in their catalogs that a membrane is being supplied "dry"; however, these membranes may contain humectants such as glycerol as a pore supporting fluid. As with bacteriostats, humectants must be removed from the membrane by soaking, flushing, or some other method that never permits the membrane to become fully dried.

Representative of the second general type of UF membrane is that obtained in accordance with the disclosures of U.S. Pat. Nos. 4,954,381 and 4,451,424, which purportedly produce integrally-skinned UF membranes with macrovoid-free matrices by increasing the viscosity of the casting solution through the addition of water soluble viscosity enhancing polymeric additives such as polyvinylpyrrolidone (PVP) or polyethyleneglycol (PEG). These membranes exhibit a skin with a pore size distribution which is too broad to be integrity-tested because of the leaching out of the polymeric additives during precipitation and washing steps, as well as during their use in the UF process. These membranes can be supplied "dry"(i.e., no free liquid present), but contain high concentrations of residual PVP or PEG. Humectants such as glycerol, PVP, PEG, and/or water and other wetting fluids may act as plasticizers to diminish friability. These materials may also act as pore supporting fluids which if removed lead to cracks and other defects in the membrane skin. Additionally, the pore size increases with the molecular weight of the extractable additive, which is in turn related to the breadth of the pore size distribution of these membranes.

Although widely used, UF membranes are recognized to suffer from some serious drawbacks. For example, nearly all UF membranes contain a humectant such as glycerol or must be maintained in a wetted state at all times, including during shipping, because the filtration properties of the membrane are unstable owing to the presence of defects. Once the humectant or other supporting liquid is removed and the membrane is dried and rewetted, the performance of the membrane is altered, and the membrane skin becomes cracked, thereby rendering the membrane useless. This means that as a practical matter, all UF membranes must be shipped along with a large amount of wetting liquid, usually water, which increases shipping costs. Further, the requirement that the membrane be maintained in a wetted state also is a substantial burden on the users who must assure that the membrane is never allowed to dry. The fact that the membranes are constantly maintained in a wetted state also means that the risk of bacterial growth is present, requiring then that a bacteriostat, or the like, be present in the wetted membrane. Unfortunately, the presence of a bacteriostat also introduces the problem of contamination of the product stream by the membrane, for once such an agent is present, it is difficult, if not impossible, to remove.

In the case of membranes containing a humectant such as glycerol, the membrane must be soaked in several changes of water or other solvent in order to remove as much of the foreign material as possible. Then, once the pore structure is supported with the solvent, the sample must never be permitted to dry out.

Another significant problem with all currently available UF membranes is the presence of significant defects in the membrane. Such defects include macrovoids, cracks, pinholes, and other defects and imperfections that either breach the skin layer or lead to failure of the membrane. The presence of such defects means, however, that although a given membrane may be rated with a removal rating that would indicate, for example, that the membrane is capable of removing materials of moderate molecular weight (e.g., between 1,000 to 500,000 daltons) from a liquid, the presence of the defects allows a given portion of the substances to pass through the membrane, which, of course, is very undesirable. Even relatively large particles such as latex spheres are known to pass through UF membrane defects.

Molecular weight cutoff is an expression of the retention characteristics of a membrane in terms of molecules of known sizes. Retention is commonly rated as that MWCO at which at least 90 percent of spherical uncharged molecules of that same molecular weight will be retained by the porous membrane, whereas less than about 50 percent of such molecules of significantly lower molecular weight will be retained. However, linear molecules with molecular weights greater than the MWCO may pass through the membrane because the effective diameter of a linear molecule is smaller than that of a spherical molecule. Linear molecules may approach a membrane pore "end on" and thread themselves through the pore. This can occur if a long chain linear molecule is aligned with the laminar flow lines of the fluid passing through the membrane. On the other hand, charged molecules less than the MWCO may not pass through the membrane due to electrostatic interactions with the membrane. In UF membranes, the MWCO ranges from about 500 or 1000 daltons up to about several million daltons corresponding to pore sizes of 10 to 200 Å.

Although a limited number of UF membranes have been recently introduced in the form of hollow fibers, with indicated nominal MWCO ratings in the 1,000 to several million dalton range, which membranes are capable of being shipped in the dry state, such membranes still suffer from the very significant problem of having defects in their structure, rendering them of only limited value.

Present-day UF membranes work on a statistical basis, i.e., as only a small portion of liquid being filtered passes through defects in the membrane, and as only a portion of all liquid being filtered contains the material to be removed, the probability is that only a small amount of the material to be removed will pass through the membrane. If, however, the material being filtered is, for example, a pharmaceutical composition, and the material to be removed is bacteria, then even the passage of only a few bacteria through the membrane in a single lot of fluid can be unacceptable.

Because of the wide and large number of applications for UF membranes, considerable effort has been spent to improve the effectiveness of such membranes, but, to date, with limited success. Many patents and articles have been published regarding the manufacture of UF membranes, some claiming them to be "defect-free", and some claiming them to be dryable, but the fact remains that no UF membrane has heretofore been produced that is both dryable and which is free of defects.

The present invention seeks to provide a filtration medium comprising a UF membrane which is free of at least some of the aforesaid problems affecting prior art UF membranes. In particular, the present invention seeks to provide a filtration medium comprising a UF membrane which is substantially defect-free and which can be fully dried without loss of its UF properties. These and other objects and advantages of the present invention, as well as additional inventive features, will be apparent from the description of the invention provided herein.

BRIEF SUMMARY OF THE INVENTION

The present invention provides a filtration medium comprising an ultrafiltration membrane and a monomer surface coating thereon of an acrylic or methacrylic acid monomer having alcohol functional groups, wherein the filtration medium after having been fully dried is characterized by having a titer reduction of at least about $10^3$ with respect to PP7 bacteriophage and a critical wetting surface tension of at least about 70 mN/m (about 70 dynes/cm). The filtration medium preferably further comprises a fibrous nonwoven web embedded in the membrane. The present invention also provides a method of filtering a fluid through the present inventive filtration medium, as well as a method of preparing such a filtration medium.

DESCRIPTION OF THE PREFERRED EMBODIMENTS

Figure 1:
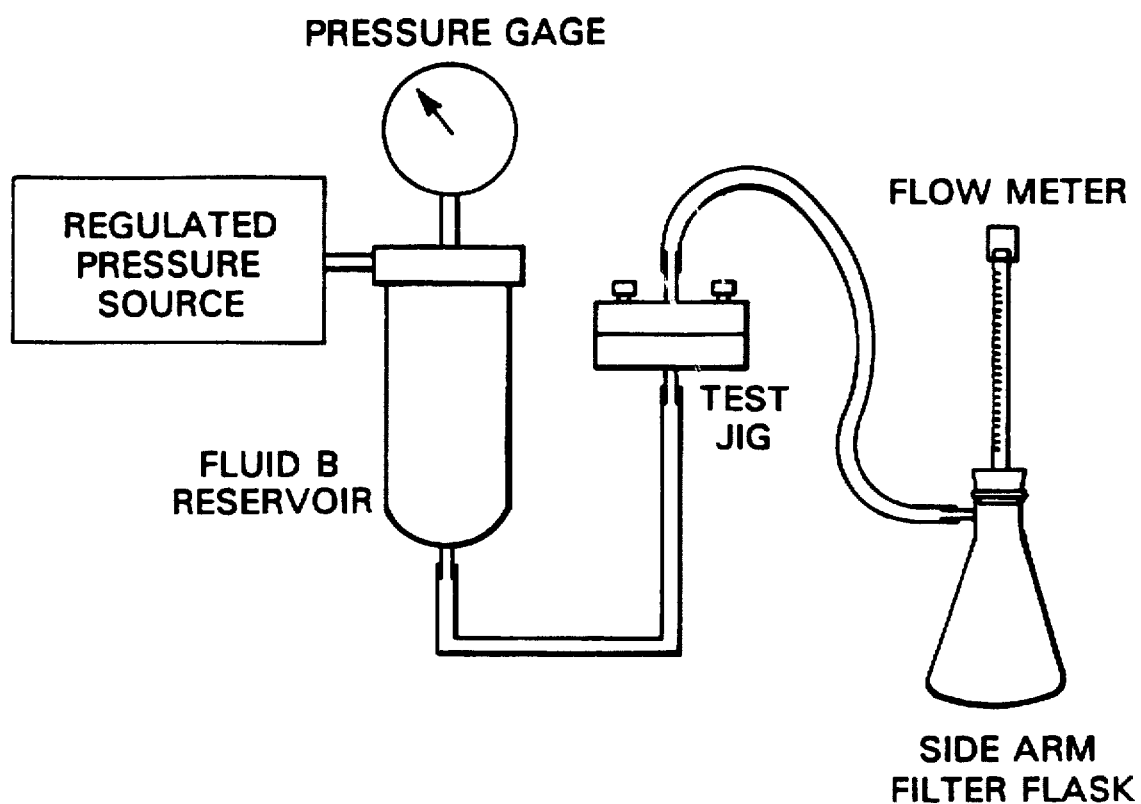
FIG. 1 is a diagram of an apparatus for measuring $K_{UF}$ in accordance with the present invention.

The present invention provides a novel filtration medium, a method of using such a filtration medium, and a method of preparing such a filtration medium. The present inventive filtration medium comprises an ultrafiltration membrane and a monomer surface coating thereon of an acrylic or methacrylic acid monomer having alcohol functional groups, wherein the filtration medium after having been fully dried is characterized by having a titer reduction of at least about $10^3$ with respect to PP7 bacteriophage and a critical wetting surface tension of at least about 70 mN/m (about 70 dynes/cm). The filtration medium preferably further comprises a fibrous nonwoven web embedded in the membrane. The present inventive method of filtration comprises passing a fluid through such a filtration medium.

The present inventive method of preparing a filtration medium comprises (a) dissolving a polymeric resin in a carrier comprising both a solvent for the resin and a nonsolvent for the resin to thereby form a solution, wherein the resin is present in an amount from about 15–20 wt. % of the solution, and the amount of nonsolvent is from about 26–34 wt. % of the solution, with the ratio of solvent to nonsolvent being from about 1.5:1 to about 2:1, (b) rapidly mixing the solution to reduce or eliminate the presence of gel particles, (c) filtering the solution to remove any gel particles that are present therein, (d) degassing the solution to remove any entrained gas, (e) casting or spinning the solution onto a support, (f) contacting the resulting cast or spun solution with a setting bath that comprises both a solvent and a nonsolvent for the resin, and (g) grafting the resulting membrane with a monomer of an acrylic or methacrylic acid monomer having alcohol functional groups such that the monomer coats the surface of the membrane so as to form a filtration medium after having been fully dried characterized by having a titer reduction of at least about $10^3$ with respect to PP7 bacteriophage and a critical wetting surface tension of at least about 70 mN/m (about 70 dynes/cm). The solution is preferably cast or spun onto a fibrous nonwoven support so as to envelope the fibrous nonwoven support.

Membrane

The ultrafiltration membrane which is a part of the present inventive filtration medium, i.e., the ultrafiltration membrane without a monomer surface coating thereon, is capable of being dried without loss of such ultrafiltration properties. Such membranes may be selectively prepared in accordance with the present invention to have any particular MWCO ratings, from about 1,000 daltons to about 500,000 daltons. Membranes with a rated MWCO of $\leq 20,000$ are capable of excluding 0.02 μm diameter, monodisperse, latex particles to rejection coefficients of >0.998. Membranes with a rated MWCO of $\leq 100,000$ are capable of excluding 0.04 μm diameter, monodisperse, latex particles to rejection coefficients of >0.998. Membranes with a rated MWCO of $\leq 500,000$ are capable of excluding 0.1 μm diameter, monodisperse, latex particles to rejection coefficients of >0.998. The membranes utilized in the context of the present invention will generally have a pore size from about 200 Å down to about 10 Å.

The membrane of the present invention may be also characterized in terms of titer reduction. In particular, the membrane utilized in the context of the present invention, i.e., the ultrafiltration membrane without a monomer surface coating thereon, after having been fully dried desirably has a titer reduction of at least about $10^4$, preferably at least about $10^6$, and more preferably at least about $10^8$, $10^{10}$, or more, with respect to PR772 coliphage and desirably has a titer reduction of at least about $10^3$, preferably at least about $10^5$, more preferably at least about $10^6$, and most preferably at least about $10^8$, $10^{10}$, or more, with respect to PP7 bacteriophage. The titer reduction of a membrane is defined as the ratio of a substance, e.g., PP7 bacteriophage, contained in the influent to that obtained in the effluent. The titer reduction values set forth herein are with respect to applied pressures of about 21 kPa (about 3 psi) and/or about 105 kPa (about 15 psi).

As the size of the PR772 phage is about 0.053 μm, and the size of the PP7 phage is about 0.027 μm, these phages provide excellent models for assessing the removal efficiency of a membrane with regard to intermediate-sized and smaller viruses. Since these biological substances are capable of rapid replication, they allow for easy detection of the most minute quantities in the filtrate of a test solution. Thus, the inability to detect any quantity of a particular such model biological substance in the filtrate of a test solution is excellent confirmation of the fact that the particular membrane actually prevented all of the biological substance in the challenge liquid from passing through the membrane. Moreover, since the quantity of viruses found as contaminants in most commercial processes rarely exceeds about $10^4$/ml, the ability of the present inventive membrane to have a titer reduction of $10^4$ or higher with respect to the PP7 bacteriophage can provide nearly absolute assurance of the removal of all viruses from a wide variety of liquids, particularly those involved in commercial processing, e.g., pharmaceutical production.

The membrane utilized in the context of the present invention, i.e., the ultrafiltration membrane without a monomer surface coating thereon, after having been fully dried can be further characterized as having a $K_{UF}$ value of from about 35 kPa to about 830 kPa (about 5 psi to about 120 psi), preferably from about 70 kPa to about 830 kPa (about 10 psi to about 120 psi), more preferably from about 140 kPa (about 20 psi), or even about 210 kPa (about 30 psi), to about 830 kPa (about 120 psi), determined using 1-butanol, saturated with water, as the wetting liquid, and water, saturated with 1-butanol, as the displacing liquid. The immiscible phases are mutually saturated to ensure that the interfacial tension between the liquids does not change due to dissolution of one phase into the other. Other factors such as temperature should also remain relatively constant during the test procedure so as to avoid substantial changes in the interfacial tension between the immiscible liquids. The $K_{UF}$ test method is described in U.S. patent application Ser. No. 07/882,473, now U.S. Pat. No. 5,480,554 as well as in the published U.K. counterpart thereto, U.K. Patent Application No. 9308385 (Publication No. 2266851).

Since the membrane utilized in the present inventive filtration medium is essentially responsible for the removal efficiency of the filtration medium, i.e., the presence of the monomer coating and/or support material does not adversely contribute to the removal efficiency of the filtration medium, the present inventive filtration medium can be characterized by the same rejection characteristics or removal efficiencies recited above for the membrane per se.

Membrane Preparation

A method of preparing the membrane utilized in the present inventive filtration medium comprises dissolving a polymeric resin in a carrier comprising both a solvent for the resin and a nonsolvent for the resin to thereby form a solution, wherein the resin is present in an amount from about 15–20 wt. %, and the amount of nonsolvent is from about 26–34 wt. %, preferably about 28–34 wt. %, and more preferably about 30–34 wt. %, of the solution, with the ratio of solvent to nonsolvent being from about 1.5:1 to about 2:1, rapidly mixing the solution under high shear conditions to reduce or eliminate the presence of gel particles, filtering the solution to remove any gel particles that are present, degassing the solution to remove any entrained gas, casting or spinning the solution onto a support, and contacting the resulting cast or spun solution with a setting bath that comprises both a solvent and a nonsolvent for the resin.

An improved method of preparing any ultrafiltration or membranous structure can be utilized in the context of the present invention. That method involves casting or extruding an initial solution comprising a polymeric solute, a solvent therefor, and optionally a nonsolvent, under a set of process conditions, optionally onto or into a setting bath, containing a nonsolvent for the polymer, and optionally a solvent therefor, to form a desired membrane, thoroughly wetting a portion of the membrane to be tested with a wetting liquid that is capable of fully wetting the membrane, placing a displacing liquid that is immiscible with the wetting liquid in contact with the upstream side of the wetted membrane, applying increasing pressure to said displacing liquid and measuring the flow of displacing liquid that passes through the membrane as a function of the applied pressure, wherein the displacing liquid is substantially insoluble in the wetting liquid and the interfacial tension between the wetting liquid and the displacing liquid is about 10.0 mN/m (about 10.0 dynes/cm) or less, and adjusting one or more of the following process variables (1) the composition of the initial solution, (2) the composition of the setting bath, (3) the rate at which the casting resin is mixed, and (4) the casting solution temperature, or the spinning temperature, in response to the measurement.

By following the principles of the present invention, it is possible to make UF membranes possessing the afore-described properties, including the freedom from major defects, which breach the skin of the membrane.

Polymer

Any suitable polymer can be used to prepare the membrane utilized in the present inventive filtration medium. Preferred polymers include the polysulfones, particularly polyethersulfones and polyphenylsulfones. For sake of brevity, the invention will be described in terms of aromatic polysulfones, particularly polyethersulfones, with the understanding that the invention described herein has broader application to other membrane structures.

Preferred polysulfones for forming the membrane include aromatic polysulfones comprised of recurring units of the general formulae I, II, and III.

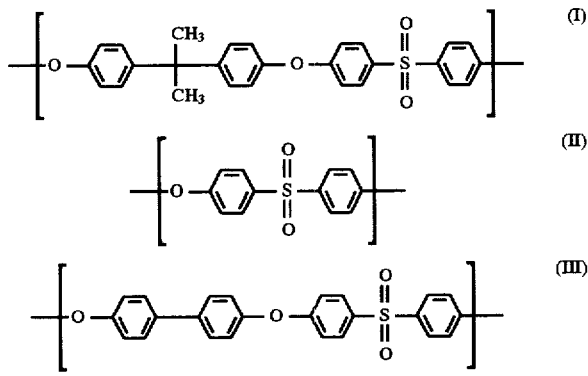

The polysulfones represented by formulae I, II, and III are available as Udel® (Union Carbide), Victrex® (ICI), and Radel® (Union Carbide), respectively. The aromatic polyethersulfone of formula II above is particularly preferred within the context of the present invention. While the polysulfone resins can have any suitable molecular weight, these aromatic polysulfone resins preferably have a number average molecular weight of 20,000 to 100,000 daltons, most preferably from about 30,000 to about 50,000 daltons.

Other suitable polysulfones and their preparation are disclosed in Cudby et al., "Synthesis of Poly(arylene sulphones) by Polycondensation of Arylsulphonyl Chlorides under Friedel-Crafts Conditions," *Polymer*, 6, 589 (1965), Cudby et al., "Structures of the Poly(diphenylene ether sulphones) Obtained by Polysulphonylation," *Polymer*, 9, 265 (1965), U.K. Patent 1,016,245, and U.S. Pat. Nos. 4,008,203, 4,105,636, and 4,108,837.

Casting Solution

The solvent system (vehicle) for the resin, such as polyethersulfone, comprises at least one solvent and at least one nonsolvent. Examples of suitable solvents include dimethylformamide (DMF), N,N-dimethylacetamide (DMAC), dimethylsulfoxide (DMSO), N-methylpyrrolidone (NMP), and formylpiperidine (FP). Preferred non-solvents are propionic acid (PA), butyric acid (BA), and isobutyric acid (IBA).

The preferred casting or spinning solution comprises about 15–20 wt. % resin, such as a polyethersulfone, particularly an aromatic polyethersulfone, more preferably about 16–19 wt %, and most preferably about 17–18 wt. %. Further, the ratio of solvent to nonsolvent is preferably from about 1.5:1 to about 2:1, most preferably from about 1.5:1 to about 1.9:1, and usually about 1.7:1.

Gelation Bath

A gelation bath is used which consists of a non-solvent medium containing nonsolvent and an appreciable amount of solvent. Pore size increases as the concentration of solvent in the membrane gelation bath is increased. The composition of the membrane gelation bath varies with the nature of the solvent. Usually about 10–50 wt. % of solvent is present in the membrane gelation bath, with the balance being nonsolvent, preferably water together with whatever nonsolvent is employed in the casting resin solution, usually monocarboxylic acids containing 3 or 4 carbon atoms. For the solvents dimethylacetamide or N-methylpyrrolidone, the preferred concentration of solvent is about 20–45 wt. %. Organic solvents are the generally preferred additives to the membrane gelation baths. Preferably, the gelation bath comprises water in conjunction with the particular solvent and nonsolvent employed in the casting resin solution, especially wherein the ratio of the particular solvent to nonsolvent employed in the casting resin solution (i.e., excluding the water or other components) is about 1.5 to 2, most preferably about the same as the ratio of solvent to nonsolvent in the casting resin solution.

Other Casting Parameters

Before casting membranes, the casting solution is preferably well mixed, as with a high shear mixer, and then filtered. Such filtration ensures that the casting solution is free of contaminant particles, such as gel particles, and substantially reduces imperfections in the cast films. Filtration of the casting solution can be accomplished by any suitable means. For example, the casting solution can be suction filtered through glass microfiber, porous stainless steel, or other filter material and then passed through one or more membranes having pores with diameters of about 5 μm. In order to enable the solution to pass through the smaller pore size membranes at acceptable flow rates, it is usually necessary to apply pressure to the casting solution. The amount of pressure applied will depend upon the viscosity of the solution and the pore size of the membrane.

The casting solution is also preferably degassed prior to casting a membrane therewith. The degassing is important in that, if the casting solution is not properly degassed, the result will be a membrane with substantial defects, such as pinholes. Degassing of the casting solution can be accomplished through the use of any suitable technique.

The casting solution is then cast as a thin fluid film onto and/or into a suitable (porous or nonporous) substrate to form an overall membrane thickness of about 25–250 μm, preferably about 50–150 μm. Among the porous substrates which are useful for this invention are various non-woven and woven fabrics which are similar or identical to those used in the reverse osmosis and ultrafiltration industries. A fibrous nonwoven web is preferably utilized as the support material, and the casting solution preferably envelopes or encases the fibrous nonwoven web, most preferably so as to form a filtration medium having skinned surfaces on two sides. In addition to the flat sheet configuration, the membranes of this invention can be prepared in hollow fiber or tubular form with properties similar to those described for flat sheets.

Following gelation the membrane is washed free of solvent, e.g., by using water, and dried.

The temperature of the casting or spinning solution is generally controlled in the range of between ambient temperature and 85° C., preferably between 30°–65° C. The temperature of the coagulating liquid is generally controlled to be about ambient temperature.

The properties of the membranes may be determined by the specific properties of the selected polymer system employed, but, with careful selection and good processing technique, it is possible to attain UF membranes with physical and chemical properties appropriate for use in a wide variety of ultrafiltration and diafiltration operations.

Without limiting the breadth of the present invention, and without being bound to any particular theory, it is believed that the narrowness of the pore size distribution in the membranes is due to a number of related factors: (1) the absence of extractable polymeric additives, (2) the use of solvent vehicles containing large solvent entities, (3) the use of solutions with a low tolerance for nonsolvents, (4) the controlled nucleation of the solution by high sheer stirring, nonsolvent addition, and temperature control, (5) the removal of gel clumps from the solution by filtration, and high shear mixing, (6) the gelation of the casting solution in a nonsolvent bath which contains an appreciable concentration of solvent, and (7) the ability to rapidly and accurately measure ultrafiltration pore size and membrane integrity by the $K_{UF}$ method and to make process changes in response to those measurements.

By following the principles of the present invention, it is possible to make UF membranes possessing the aforedescribed properties. The membranes utilized in the context of the present invention may also be characterized by their substantial freedom from major defects, such as pinholes or macrovoids that are in the form of finger-like intrusions extending from one surface of the membrane to the other. In some embodiments, the membranes may also be characterized as consisting essentially of two layers, a thin skin with a narrow pore size distribution and a thick sponge-like, macrovoid free matrix. A third (transition) layer of intermediate density may also be found, between the skin and substructure layers.

Surface Modification

The UF membrane utilized in the context of the present invention, particularly when prepared from a polysulfone, e.g., an aromatic polyethersulfone, can be hydrophobic and exhibit a significant tendency to adsorb proteins and the like, which may be present in a liquid being filtered. These characteristics are undesirable inasmuch as they contribute to a higher pressure drop across the membrane and can ultimately result in the premature fouling of the membrane and/or, in certain cases, the formation of a secondary sieving layer on the surface of the membrane. In addition, the removal of proteins from the fluid being filtered may represent a loss of valuable material and/or be otherwise undesirable.

As a result, the membrane is preferably surface modified to render it hydrophilic (i.e., having a critical wetting surface tension (CWST) of at least about 70 mN/m (about 70 dynes/cm), preferably at least about 72 mN/m (about 72 dynes/cm), and more preferably at least about 74 mN/m (about 74 dynes/cm), e.g., about 74–78 mN/m (about 74–78 dynes/cm), as determined by the CWST test disclosed in U.S. Pat. No. 4,880,548, and thereby less susceptible to protein adsorption and fouling.

Such surface modification of the membrane can be carried out in any suitable manner and is preferably accomplished by graft polymerizing a suitable monomer onto the surface of the membrane. Preferred examples of such monomers include acrylic or methacrylic monomers having alcohol functional groups, such as, for example, hydroxyethylacrylate (HEA), hydroxyethylmethacrylate (HEMA), hydroxypropylacrylate (HPA), hydroxypropylmethacrylate (HPMA), and combinations thereof, particularly HPA and/or HEMA.

Any suitable means may be used to polymerize the suitable monomers onto the membrane. Radiation grafting is the preferred technique to achieve such a result. The source of radiation can be from radioactive isotopes like Cobalt 60, Strontium 90, and Cesium 137, or from machines like x-ray machines, electron accelerators, and ultraviolet equipment. Preferably, however, the radiation is in the form of electron beam radiation. It has been found that, by using this form of radiation, a very uniform distribution of radiation can be provided. This in turn results in a final product which is grafted more uniformly as compared to membranes which are grafted using other radiation sources, e.g., Cobalt 60.

Grafting will typically be achieved by either irradiating the membrane and then exposing it to a suitable solution of the monomer or irradiating the membrane while it is exposed to a suitable solution of the monomer. Regardless of which procedure is used, the grafting should be conducted in the absence of oxygen, e.g., under a nitrogen atmosphere, since oxygen will react with the reactive sites created by radiation exposure, thereby lowering the number of sites available for the desired polymer bonding. If the membrane is irradiated prior to immersion in the monomer solution, the membrane should contact the monomer solution as quickly as possible to avoid undesirable reactions resulting in the loss of reactive sites for bonding the polymer to the surface of the membrane. The monomer solution can comprise any suitable concentration of the monomer to be graft polymerized, typically 1–10 vol. % monomer in a solvent system, generally water by itself or with a suitable alcohol such as t-butyl alcohol. The preferred monomer solution in the context of the present invention is 1.5 vol. % HPA, 25 vol. % t-butyl alcohol, and 73.5 vol. % deionized water. The details and parameters of the polymer grafting of membranes is well known in the art.

While the graft polymerization can be carried out in the absence of crosslinking agents, it is preferred that such crosslinking agents be used, particularly when the aforementioned acrylate monomers are graft polymerized onto the surface of the membrane. Any suitable crosslinking agent can be used in the context of the present invention. Suitable crosslinking agents include di- or poly-acrylates and methacrylates of diols and polyols, particularly linear or branched aliphatic diols such as ethylene glycol, 1,2-propylene glycol, diethylene glycol, dipropylene glycol, dipentylene glycol, polyethylene glycol, polypropylene glycol, polytetramethylene-oxide glycol, and poly(ethylene oxide-copropylene-oxide)glycol, as well as triol acrylates such as trimethylolpropane triacrylate. Examples of other crosslinking monomers that may be used in the instant invention include allyls, maleimides, unsaturated dicarboxylic acids, aromatic vinyl compounds, polybutadienes, and trimellitic acid esters. Other suitable crosslinking agents are described in U.S. Pat. Nos. 4,440,896, 4,753,988, 4,788,055, and 4,801,766.

Polyethylene glycol dimethacrylates (PEGDM) wherein the molecular weight of the polyethylene glycol is about 200 to about 600, are preferred crosslinking agents in the context of the present invention. Polyethylene glycol 600 dimethacrylate (PEG 600 DM), especially in conjunction with radiation grafting HPA onto the surface of the membrane, is the most preferred crosslinking agent.

The crosslinking agent can be utilized in any suitable amount. Typically, the crosslinking agent will be added to the grafting solution in an amount of about 0.025 vol. % to about 5 vol. %, more typically in an amount of about 0.05 vol. % to about 2 vol. %. Thus, for example, a monomer solution containing 1.5 vol. % HPA in a mixture of water and t-butyl alcohol preferably contains about 0.5 vol. % PEG 600 DM as the crosslinking agent.

The resulting surface modified membrane, i.e., the present inventive filtration medium, after having been fully dried is preferably characterized by substantial transmission through the filtration medium of proteins with a molecular weight of about 50,000 daltons or less, more preferably about 70,000 daltons or less. The present inventive filtration medium can be prepared such that there is substantial transmission through the filtration medium of proteins with a molecular weight of about 100,000 daltons or less, even about 200,000 daltons or less.

In particular, the present inventive filtration medium after having been fully dried is preferably characterized by a bovine serum albumin (BSA) protein transmission of at least about 85%, more preferably at least about 90%, and most preferably at least about 95%, and even at least about 98%, tested using a 47 mm diameter disc to filter 50 ml of a 5 mg/ml BSA solution at about 21 kPa (about 3 psi) and/or at about 105 kPa (about 15 psi) applied pressure. Similarly, the membrane is preferably characterized by an immune serum globulin (IgG) protein transmission of at least about 40%, more preferably at least about 50%, and most preferably at least about 60%, and even at least about 70%, tested using a 47 mm diameter disc to filter 40 ml of a 0.5 mg/ml IgG solution at about 21 kPa (about 3 psi) and/or at about 105 kPa (about 15 psi) applied pressure.

These significant protein transmission characteristics of the present inventive filtration medium can be present in conjunction with the excellent viral titer reduction characteristics of the present inventive filtration medium. Thus, the present inventive filtration medium can be characterized as having the aforesaid viral titer reductions in the presence of proteins, e.g., 5 mg/ml BSA. In particular, the present inventive filtration medium after having been fully dried preferably has a titer reduction of at least about $10^6$ with respect to PR772 coliphage and at least about $10^3$, more preferably at least about $10^5$, most preferably at least about $10^6$, and even at least about $10^8$, $10^{10}$, or more, with respect to PP7 bacteriophage in the presence of 5 mg/ml BSA. Accordingly, the present inventive filtration medium is capable of removing the smallest viruses from a fluid despite the presence of proteins and preferably while allowing the desirable proteins in that fluid to pass through the filtration medium.

Illustrative Uses

The present inventive filtration medium can be used in any suitable application, including applications in which conventional UF membranes are currently being used. The present inventive filtration medium is particularly useful in molecular separations and in UF and DF applications in biological systems. In view of the excellent removal characteristics and titer reduction of the filtration medium with respect to viruses and similar sized particulates, particularly in conjunction with the excellent protein transmission characteristics of the filtration medium, the present inventive filtration medium has particular utility in the filtration of pharmacological liquids and the like, although the present inventive filtration medium can be used to filter any suitable fluid.

Thus, the present invention provides a process for filtering a fluid comprising causing the fluid to flow through the present inventive filtration medium. Such a process can include the filtration of fluids to remove proteins, for example, when the membrane has a MWCO of from about 1,000 to about 30,000 daltons. Filtration of fluids to selectively remove proteins or viruses, such as from blood and blood serum, is also possible, as when the membrane has a MWCO of about 500,000 daltons.

The ability of the membrane utilized in the context of the present invention to be integrity tested with relative ease, and to be consistently prepared on a commercial basis, enables the present inventive filtration medium to provide a predictable removal rating for given substances. Moreover, the excellent removal characteristics of the present inventive filtration medium are obtained at a reasonable pressure drop across the filtration medium. Thus, to the extent that the present inventive filtration medium can be used in applications in which conventional UF membranes are currently being utilized, the present inventive filtration medium will prove much more desirable than, and will outperform, conventional UF membranes in those same applications.

The present inventive filtration medium can be used in suitable filters, filtration cartridges, and the like. Of course, in view of the excellent removal efficiency of the present inventive filtration medium, as well as its low susceptibility to protein adsorption, the present inventive filtration medium can be used in dead-end filtration applications, as well as in tangential, cross-flow, and dynamic filtration applications.

The present inventive filtration medium in expected to be especially useful in filter elements, such as filter cartridges, which are generally described in U.S. Pat. No. 4,340,479. Preferred filter elements utilizing the present inventive filtration medium comprise the present inventive filtration medium in sheet form, wherein the sides of the filtration medium have been overlapped and sealed to form a tubular configuration having an exterior surface, an interior, and two ends, and end caps sealed to the ends of the tube, wherein at least one of the end caps has a central aperture providing access to the interior of the tube, and all of the seals are fluid-tight. The present inventive filtration medium is preferably corrugated in such a filter element so as to provide a large membrane surface area for the volume of the filter element. The filter element can comprise a single filtration medium of the present invention or can comprises multiple such filtration media adhered together. The other aspects of the filter element may be of any suitable construction and prepared from any suitable material. For example, the end caps can be prepared from a suitable polymeric material, such as polyester, particularly, polybutylene glycol terephthalate or polyethylene glycol terephthalate. The filter element can be constructed using techniques which are well-known in the art.

The following examples further illustrate the present invention and, of course, should not be construed as in any way limiting its scope.

EXAMPLES 1–9

A mixture of N,N-dimethylacetamide (DMAC) and propionic acid (PA) in a ratio of between 1.5 to about 2.0 parts of DMAC to one part of PA was used to dissolve polyethersulfone resin (Ultrason® E6010 available from BASF Corporation) at 17 wt. % solids. The polyethersulfone resin was combined with the DMAC/PA solvent system in a water jacketed resin kettle and maintained at a constant temperature of 50° C. while mixing for not less than 16 hours. The resulting solution was allowed to cool to room temperature during which time it was filtered and then deaerated under vacuum.

A quantity of the resin solution sufficient for doctoring a film having dimensions roughly 125 μm thick×25 cm long× 20 cm in width (roughly 5 mils thick×10 inches long ×8 inches in width) was applied to a glass plate, and a film was drawn. The glass plate containing the drawn film was then immersed in a setting bath containing a mixture of DMAC, PA, and water. Setting bath compositions were such that the ratio of the particular solvent and nonsolvent in the casting resin solution, i.e., the ratio of DMAC:PA, was the same in the setting bath as in the casting resin solution. The concentration of water in the setting baths was varied between 25 and 65 wt. %, with the balance of the bath composed of DMAC and PA. After the membrane had set, it was removed from the bath, water washed, and dried in an oven at a temperature of 100° C. for about 10 minutes.

Table 1 sets forth casting resin and bath compositions, along with the $K_{UF}$ characteristic pressures and MWCOs for membranes prepared using the procedure described above.

TABLE 1

| | Casting Solution | | | | | | Membrane Parameters | |
|---|---|---|---|---|---|---|---|---|
| | Parameters | | | Casting Bath | | | $K_{UF}$ | |
| Ex. | % PES | % DMAC | % PA | % H₂O | % DMAC | % PA | (kPa) [psi] | MWCO |
| 1 | 17 | 52 | 31 | 65 | 22 | 13 | 434 [63] | 18K |
| 2 | 17 | 52 | 31 | 45 | 35 | 20 | 276 [40] | 45K |
| 3 | 17 | 52 | 31 | 25 | 47 | 28 | 152 [22] | 106K |
| 4 | 17 | 55 | 28 | 65 | 23 | 12 | 434 [63] | 18K |
| 5 | 17 | 55 | 28 | 45 | 36 | 19 | 276 [40] | 45K |
| 6 | 17 | 55 | 28 | 25 | 49 | 25 | 152 [22] | 106K |
| 7 | 17 | 50 | 33 | 59 | 25 | 16 | 317 [46] | 36K |
| 8 | 17 | 50 | 33 | 45 | 33 | 22 | 255 [37] | 51K |
| 9 | 17 | 50 | 33 | 25 | 45 | 30 | 159 [23] | 100K |

Figure 3:
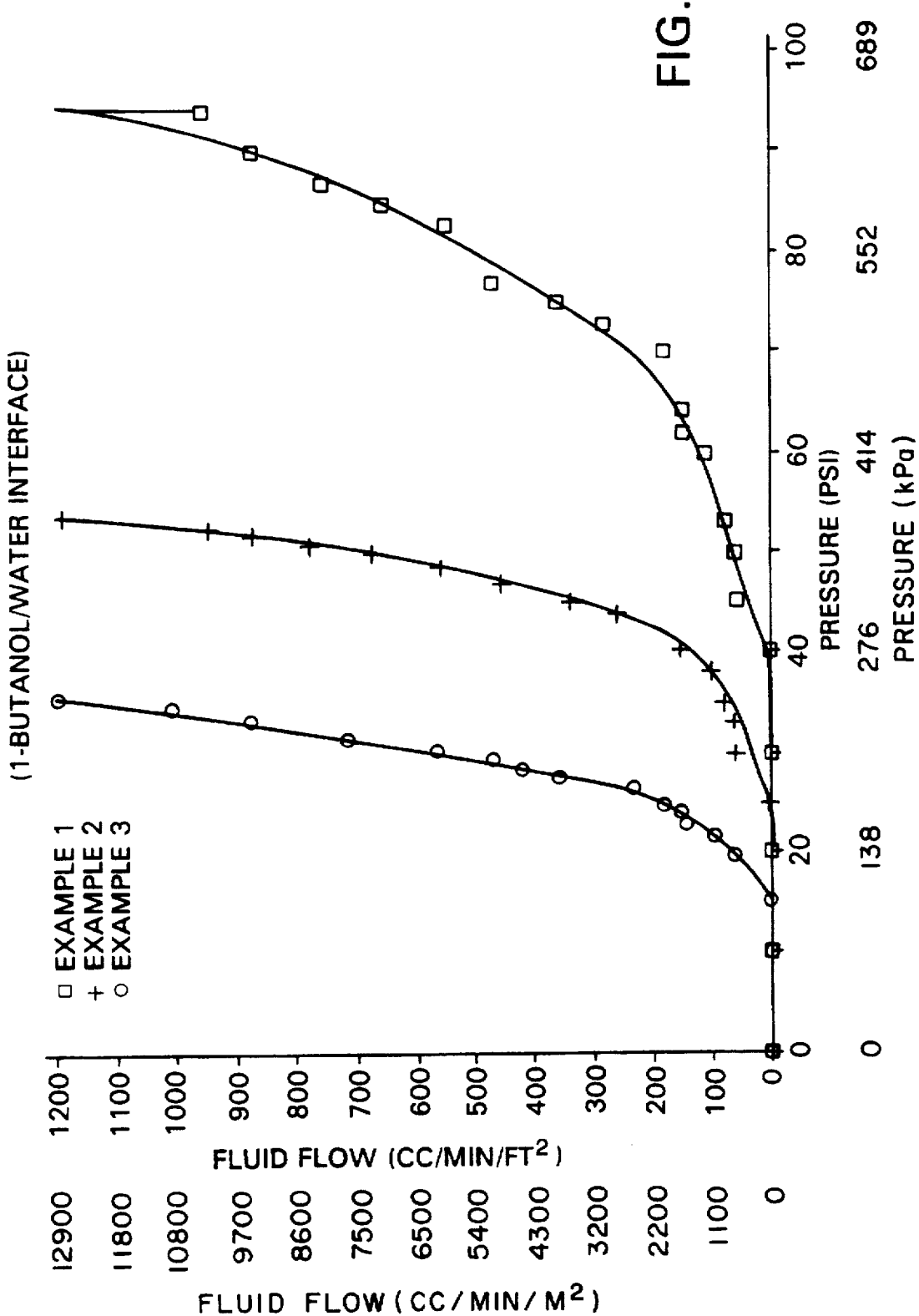
FIG. 3 is a graph showing the $K_{UF}$ plots for Examples 1–3 herein.
Figure 4:
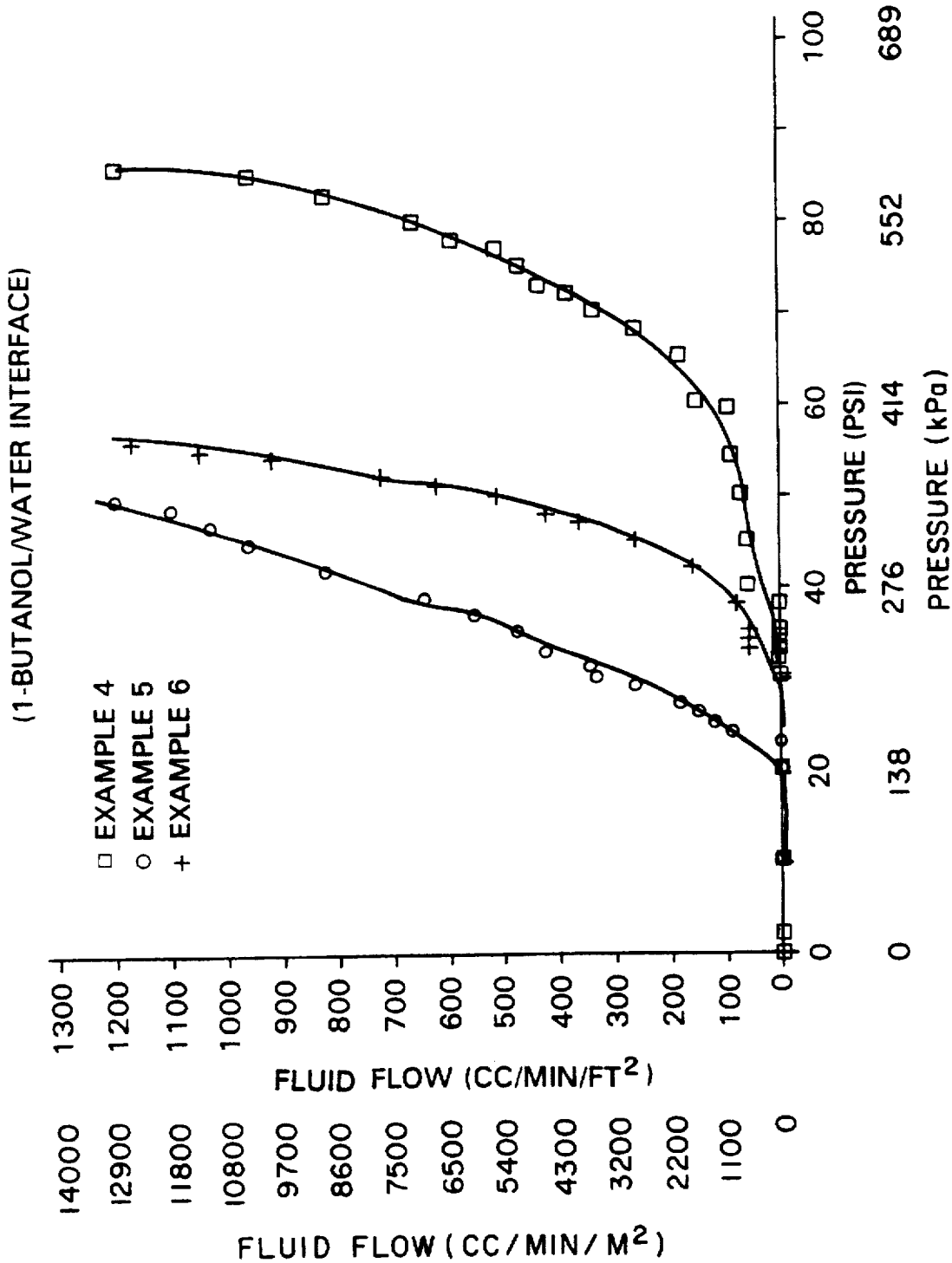
FIG. 4 is a graph showing the $K_{UF}$ plots for Examples 4–6 herein.
Figure 5:
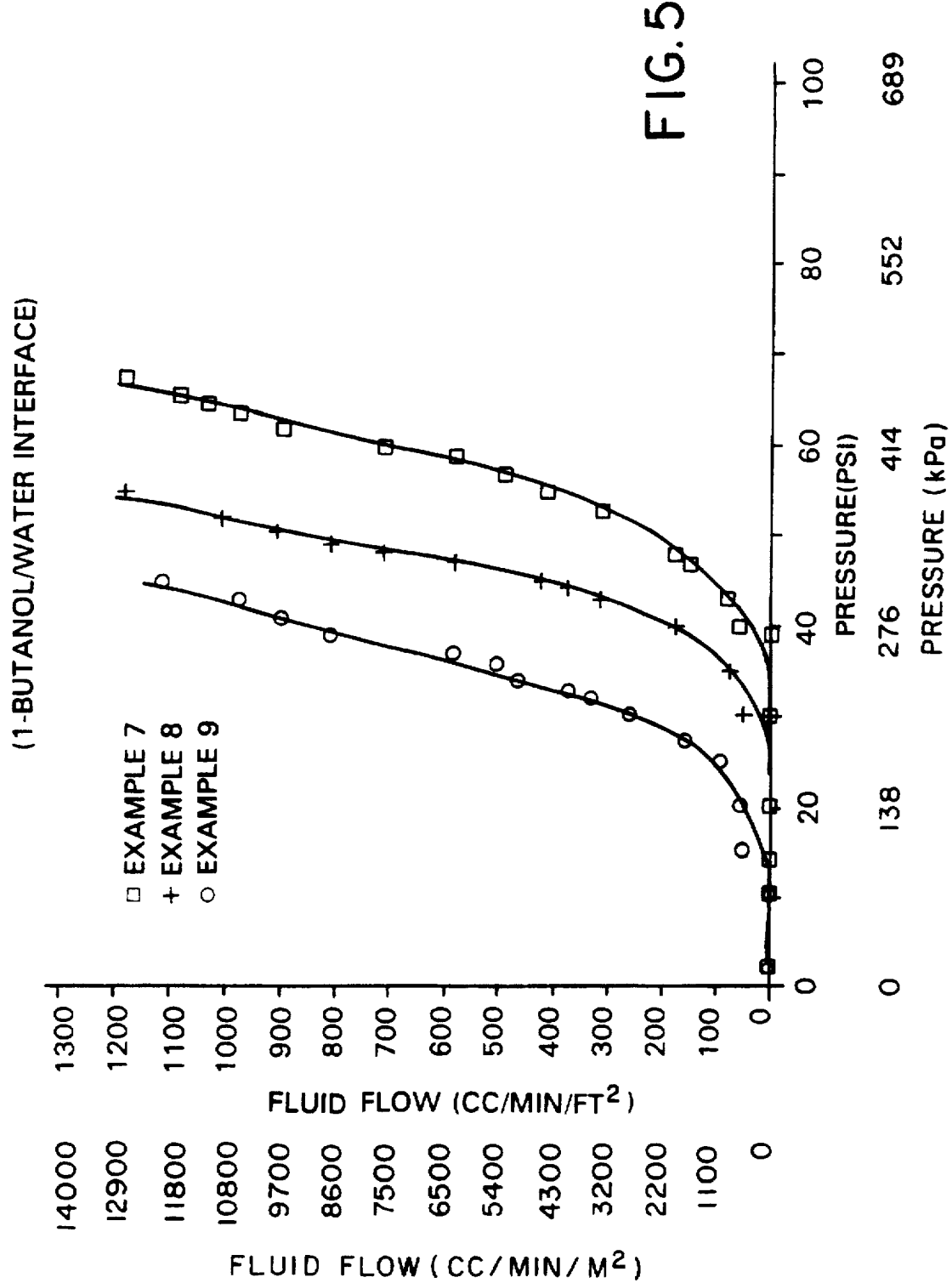
FIG. 5 is a graph showing the $K_{UF}$ plots for Examples 7–9 herein.
Figure 8:
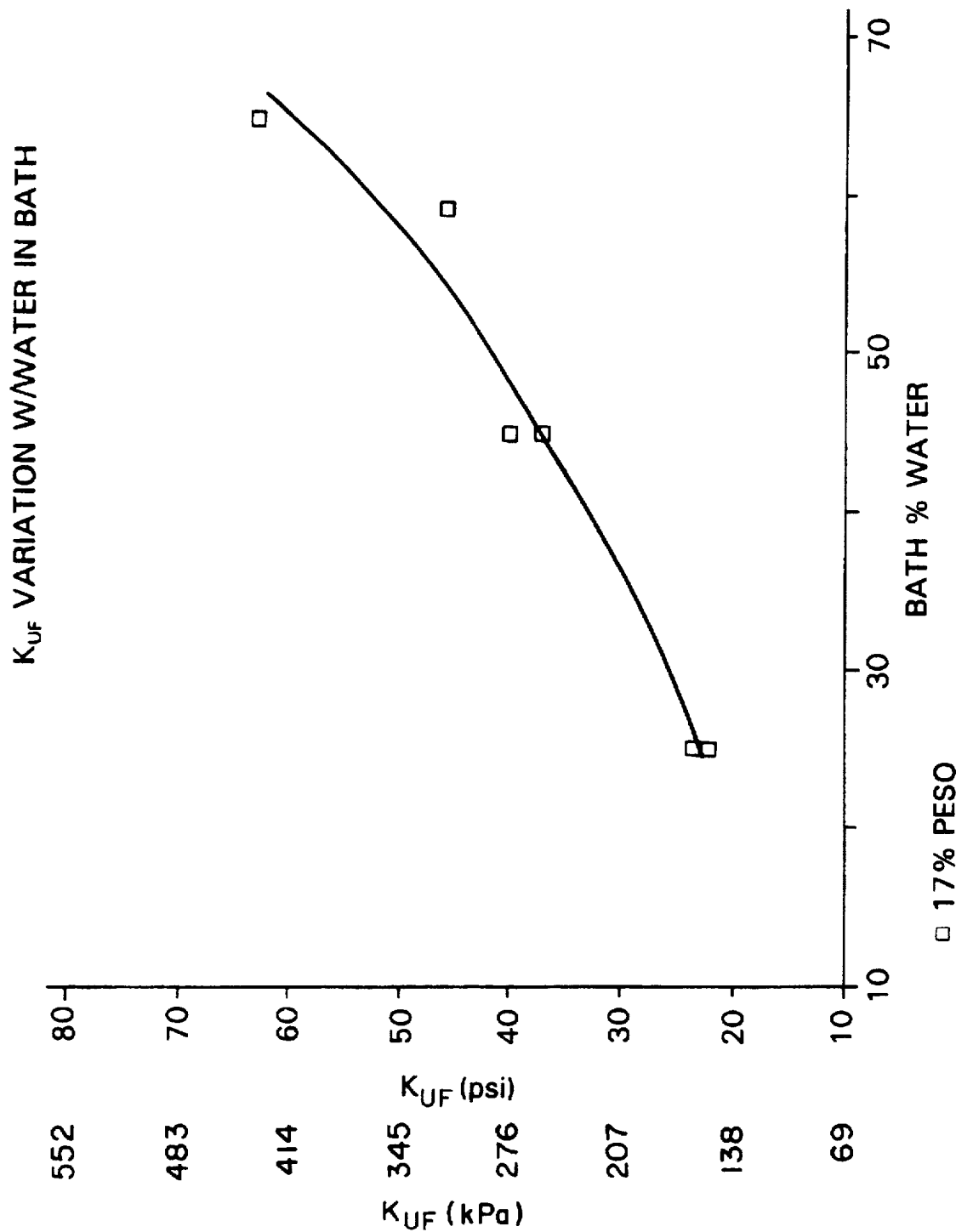
FIG. 8 is a graph showing the relationship between the concentration of nonsolvent in the casting bath and resulting $K_{UF}$ values of the membranes.

Notes:
all solutions cast at room temperature; DMAC:PA solvent:nonsolvent ratios for examples 1–3, 4–6, and 7–9 were 1.7:1; 1.92:1, and 1.5:1, respectively All the $K_{UF}$ data set forth herein was obtained, using the apparatus depicted in FIG. 1, at ambient temperature using 1-butanol saturated with water as the wetting fluid and water saturated with 1-butanol as the displacing fluid. FIGS. 3–5 are the $K_{UF}$ curves measured for each sample. As can be seen from the $K_{UF}$ curves, for any particular casting resin composition, the pore size of the membrane can be varied by varying the concentration of water in the bath. This is illustrated in FIG. 8.

By using the $K_{UF}$ test method it is shown that the membranes of the present invention, as illustrated by Examples 1–9, had $K_{UF}$ values within the range from about 70 kPa to about 700 kPa (about 10 psi to about 100 psi).

EXAMPLES 10–12

A master resin solution was prepared by dissolving polyethersulfone resin (Ultrason® E6010 available from BASF Corporation) at a concentration of 25.85 wt. % solids in DMAC at a temperature of 65° C. The master resin solution was then mixed under high shear conditions using a Type PT45/80 Polytron[R] mixer (Kinematica GmbH, Switzerland, which is distributed in the U.S. by Brinkmann Instruments, Westbury, N.Y.) to break up any undissolved polymer gels by mixing for about 1 minute at a high speed during which time the master resin temperature increased to about 80° C.

A quantity of the master resin solution, 393.2 g, was transferred to a water jacketed-flask. The resin temperature was controlled in the flask at 65° C. during which time 171.6 g of propionic acid was added to the transferred resin while mixing with a propeller type agitator. This resulted in a casting solution containing 18 wt. % polyethersulfone resin, 51.6 wt. % DMAC, and 30.4 wt. % PA.

The above solution was permitted to mix at 65° C. for about one half hour using the propeller type agitator. The casting solution was then, allowed to cool to 30° C. over a 2 hour period while mixing slowly. The casting resin solution was then removed from the jacketed flask and mixed with the Polytron mixer for about 40 sec during which time the temperature increased to 55° C. The solution was then filtered through a 5 μm nylon membrane. The resin was allowed to cool to room temperature and was then deaerated. Samples were cast into setting baths containing 25, 45, and 65 wt. % water, with the balance of the bath being composed of DMAC and PA in a ratio of 1.7 parts of DMAC, by weight, to 1 part of PA.

Figure 6:
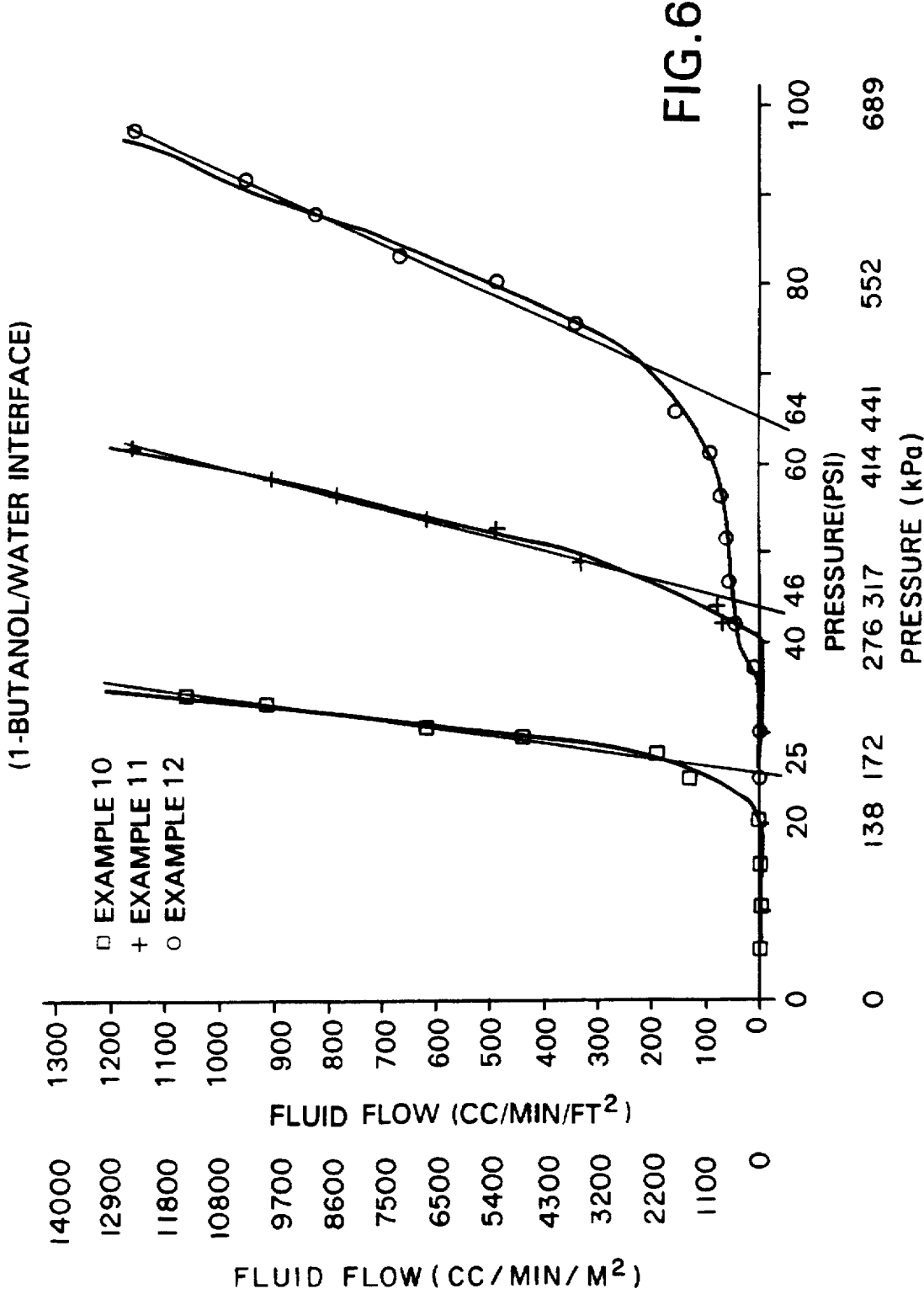
FIG. 6 is a graph showing the $K_{UF}$ plots for Examples 10–12 herein.

Table 2 summarizes the casting conditions and membrane characteristics, while FIG. 6 is a graph of the resulting $K_{UF}$ curves for the membranes.

TABLE 2

| | Casting Solution | | | Casting Bath | | | Membrane Parameters | |
|---|---|---|---|---|---|---|---|---|
| | Parameters | | | Parameters | | | $K_{UF}$ | |
| Ex. | % PES | % DMAC | % PA | % H₂O | % DMAC | % PA | (kPa) [psi] | MWCO |
| 10 | 18 | 52 | 30 | 25 | 47 | 28 | 172 [25] | 90K |
| 11 | 18 | 52 | 30 | 45 | 35 | 20 | 296 [43] | 40K |
| 12 | 18 | 52 | 30 | 65 | 22 | 13 | 441 [64] | 18K |

Notes:
all solutions cast at room temperature and with a DMAC:PA solvent:nonsolvent ratio of 1.7:1

By varying the resin concentration of the casting solution in the range between about 15 and 20 wt. % solids, while maintaining a ratio of DMAC:PA of between 1.5:1 and 2:1, and using the $K_{UF}$ test method, it is shown that the membranes had $K_{UF}$ values from about 70 to 700 kPa (about 10 to 100 psi) when tested using 1-butanol saturated with water as the wetting fluid and water saturated with 1-butanol as the displacing liquid. Varying the concentration of water in the bath will vary the pore size of the membrane and hence the $K_{UF}$ characteristic pressure and MWCO of the membrane.

EXAMPLE 13

Samples of commercial UF membranes, all with MWCos rated at or below 10,000, were compared with a membrane in the context of the present invention with a MWCO rating of 18,000 daltons. The abilities of the various UF membranes to exclude 0.020 and 0.038 μm diameter monodisperse latex spheres were compared using the following procedure. The ability to exclude such particles is understood to mean that such exclusion is measured to the detection limits of the present analysis which is approximately $4.5 \times 10^9$ particles per ml for a 0.038 μm diameter latex sphere and $4.5 \times 10^{10}$ particles per ml for a 0.02 μm diameter latex sphere. Should more precise measuring techniques be employed, and show that total exclusion is not achieved, such a fact would not alter the definition of exclusion as used in the present invention which is to be understood to mean total exclusion to the detection limits of the procedure as defined in this example.

A Tween® 20 surfactant solution was prepared by heating 500 ml of deionized water to 60° C. and adding 0.5 ml of Tween® 20 surfactant, with stirring for 10 minutes. The solution was cooled and subsequently used as a dispersing medium for the monodisperse latex spheres.

Monodisperse latex spheres of 0.02 μm diameter were dispersed in the Tween® 20 surfactant solution at a concentration of 0.01% latex solids, which corresponds to a number concentration of about $2.3 \times 10^{13}$ particles per ml. This solution was prepared by adding 0.5 ml of 2% latex (as supplied by the distributor Duke Scientific) to 99.5 ml of the Tween® 20 surfactant solution with stirring. A similar 0.01% latex solids dispersion was prepared using 0.038 μm diameter latex spheres (manufactured by Dow) and the Tween® 20 surfactant solution. A 0.01% dispersion of the 0.038 μm latex corresponds to a number concentration of about $3.3 \times 10^{12}$ particles per ml of dispersion.

The UF membranes were tested as 25 mm disks for the penetration of the latex spheres through the membranes during filtration tests of the 0.01% latex dispersions. Also one hollow fiber module (manufactured by A/G Technology Corporation) was tested as described below.

To prepare the commercial membranes for testing, the manufacturer's instructions regarding the removal of humectant prior to membrane usage were applied. This consisted of soaking the sample for a period of about 1 hour in Tween® 20 solution which was free of latex, during which time the fluid was changed 3 times. Soaking the membranes of the present invention and the A/G hollow fiber module was not required since they contain no humectant. The membranes were then inserted into a 25 mm disk holder, and a 5 cc syringe was filled with the 0.01% latex suspension. The fluid was forced through the filter and collected in glass vials. In the case of the A/G hollow fiber sample, the module was tested with the 0.01% latex dispersion using the testing procedure described by the manufacturer in the product literature.

Figure 9A:
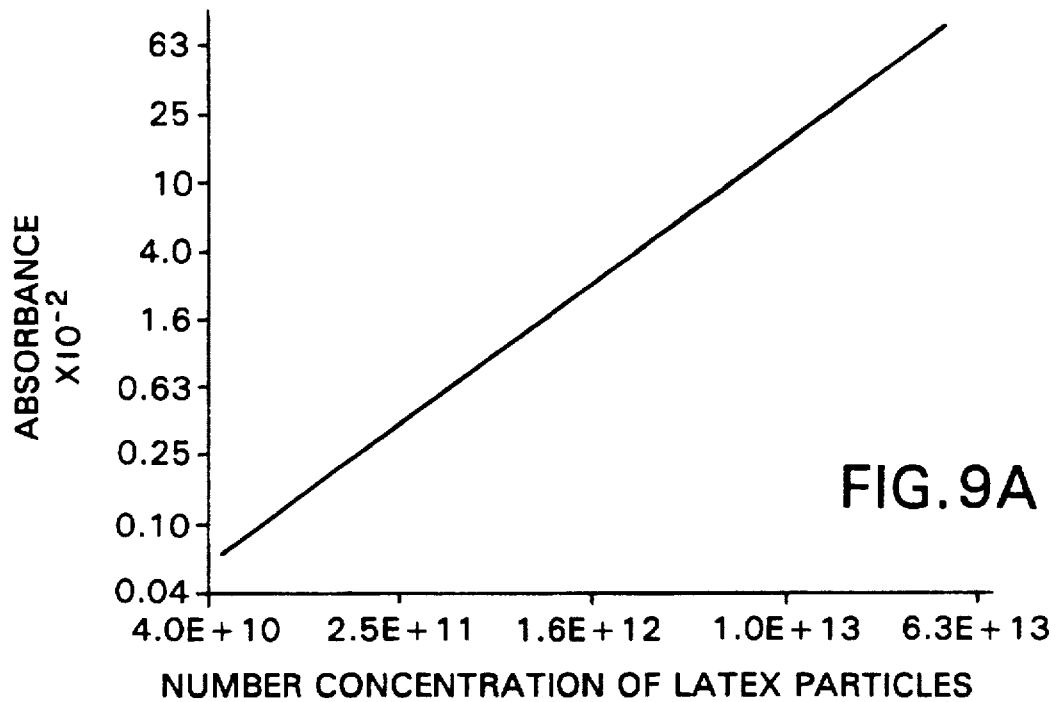
FIGS. 9A and 9B are graphs showing the relationship between UV absorbance and monodisperse latex bead concentration, as used to determine the exclusion coefficient for UF membranes, in accordance with the present invention, for 0.02 μm latex particles (FIG. 9A) and for 0.038 μm latex particles (FIG. 9B).
Figure 9B:
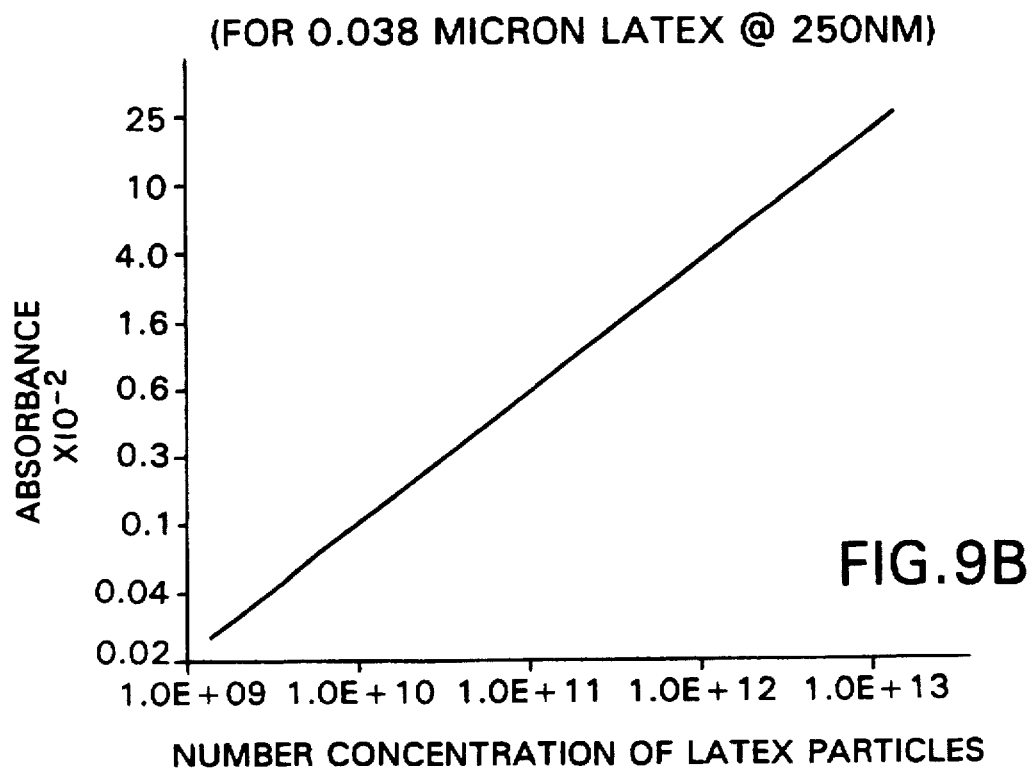

The number concentration of latex particles found in the effluents was determined by measuring the UV absorbance at a wavelength of 250 nm relative to a latex free Tween® 20 solution. The effluent latex concentration was determined from the calibration curves of FIGS. 9A and 9B, in which absorbance is plotted versus the number concentration of latex particles, i.e., 0.02 μm latex particles in FIG. 9A and 0.038 μm latex particles in FIG. 9B.

Rejection coefficients for the latex spheres were determined using the formula: rejection coefficient=1-[F/I], where F is the number concentration of latex particles detected in effluent, and I is the initial number concentration of latex particles with which the upstream side of the membrane was challenged.

Latex exclusion tests were also run on samples that were wet/dry cycled prior to the latex particle challenge. A wet/dry cycle consisted of flushing water through the membrane, drying the sample, re-wetting the sample with ethyl alcohol, again flushing water through the sample to remove the alcohol, and finally drying. This was repeated 3 times on a number of samples as indicated in Table 3, after which the membrane was challenged with latex as described above. The results of the latex exclusion tests are set forth in Table 3.

TABLE 3

| Sample Type | MWCO | # wet/dry cycles | Particle Diameter (μm) | Input Conc. (#/ml) | Effluent Conc. (#/ml) | Rej. Coeff. |
|---|---|---|---|---|---|---|
| Amicon PM10 | 10K | 0 | 0.02 | $2.3 \times 10^{13}$ | $1.3 \times 10^{12}$ | 0.94 |
| Filtron Omega | 10K | 0 | 0.02 | $2.3 \times 10^{13}$ | $2.2 \times 10^{12}$ | 0.90 |
| Millipore PTGC 10 | 10K | 0 | 0.02 | $2.3 \times 10^{13}$ | none detected | >0.998 |
| Millipore PTGC 10 | 10K | 3 | 0.02 | $2.3 \times 10^{13}$ | $2.1 \times 10^{13}$ | 0.09 |
| Millipore PTGC 10 | 10K | 3 | 0.038 | $3.3 \times 10^{12}$ | $1.3 \times 10^{12}$ | 0.61 |
| AG Hollow Fiber UFP-5-C-4 | 5K | 0 | 0.02 | $2.3 \times 10^{13}$ | $8.9 \times 10^{11}$ | 0.96 |
| Membrane of Ex. 12 | 18K | 3 | 0.02 | $2.3 \times 10^{13}$ | none detected | >.998 |

The foregoing results clearly show that the membranes of the present invention can be wet/dry cycled and will still retain the ability to exclude 0.02 μm particles. None of the commercially available UF membranes which were tested was able to exclude 0.02 μm particles after the membranes were wet/dry cycled. In fact, the Millipore PTGC 10 membrane was shown to pass even 0.038 μm particles after wet/dry cycling. Additionally, most of the samples listed in Table 3, with the exception of the Millipore PTGC 10 and the membrane of the present invention, cannot exclude 0.02 μm latex particles even when they have not been wet/dry cycled at all.

EXAMPLE 14

Figure 7:
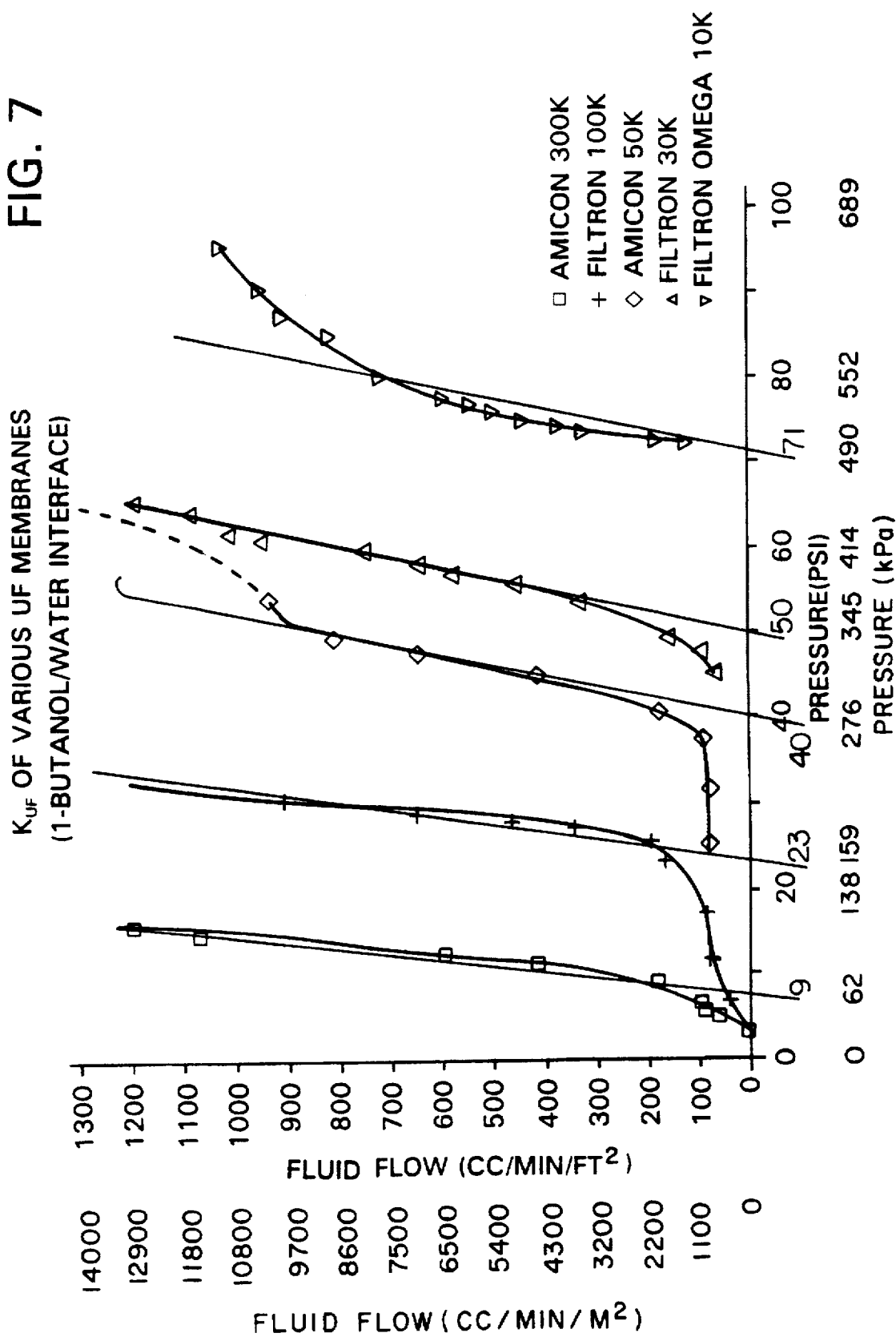
FIG. 7 is a graph showing the $K_{UF}$ plots for several commercial UF membranes.

FIG. 7 was obtained by measuring the $K_{UF}$ curves for a variety of commercially available UF membranes. The $K_{UF}$ characteristic pressures of these samples were determined from the curves of FIG. 7 using the method described above. Table 4 lists the $K_{UF}$ values so obtained along with the rated MWCOs for the membranes.

TABLE 4

| $K_{UF}$ (kPa) [psi] | $1/K_{UF}$ (kPa$^{-1}$) | [psi$^{-1}$] | Rated MWCO (Daltons) | Membrane Type |
|---|---|---|---|---|
| 62 [9.0] | 0.016 | [0.11] | 300000 | Amicon 300K |
| 159 [23.0] | 0.006 | [0.04] | 100000 | Filtron 100K |
| 276 [40.0] | 0.004 | [0.03] | 50000 | Amicon 50K |
| 345 [50.0] | 0.003 | [0.02] | 30000 | Filtron 30K |
| 490 [71.0] | 0.002 | [0.01] | 10000 | Filtron 10K |

Figure 2:
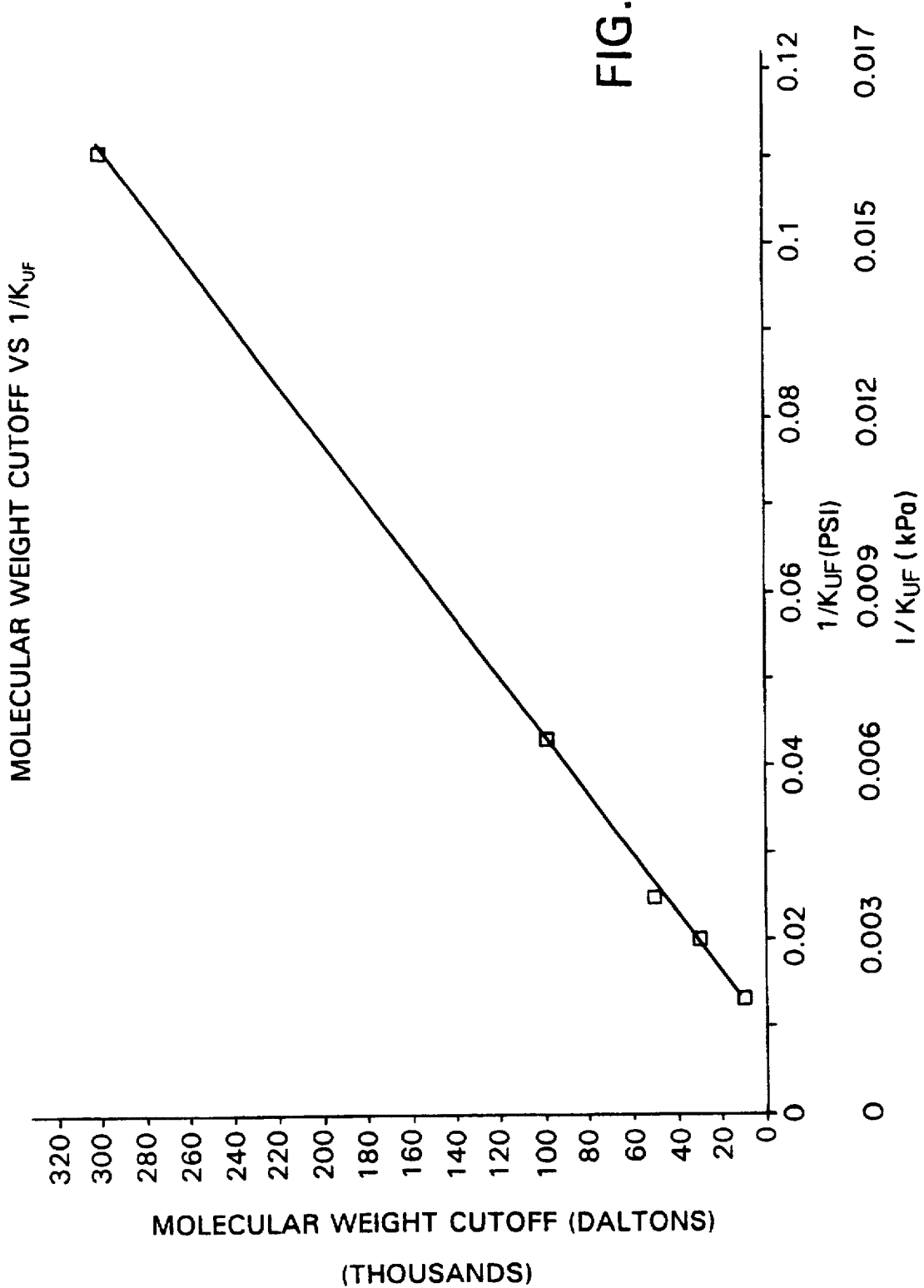
FIG. 2 is a graph showing the correspondence between MWCO and the reciprocal of $K_{UF}$ values determined in accordance with the present invention.

FIG. 2 was obtained by taking the data from Table 4 and plotting the MWCO versus $1/K_{UF}$. As can be seen from the graph, the result is a linear relationship that permits the determination of the MWCO by simply measuring the $K_{UF}$ characteristic pressure of the membrane. The $K_{UF}$ test thus represents a major advance in the characterization and integrity testing of UF membranes.

EXAMPLE 15

A $K_{UF}$ curve was obtained on a sample prepared in the context of the present invention by using the procedure described in Example 11. The sample was wet/dry cycled once using the method of wet/dry cycling described in Example 13. Similarly, a Filtron Omega membrane with a rated MWCO of 100,000 daltons was $K_{UF}$ tested before and after a single wet/dry cycle. FIGS. 10A–B and 11A–B are the resulting $K_{UF}$ curves.

Figure 10A:
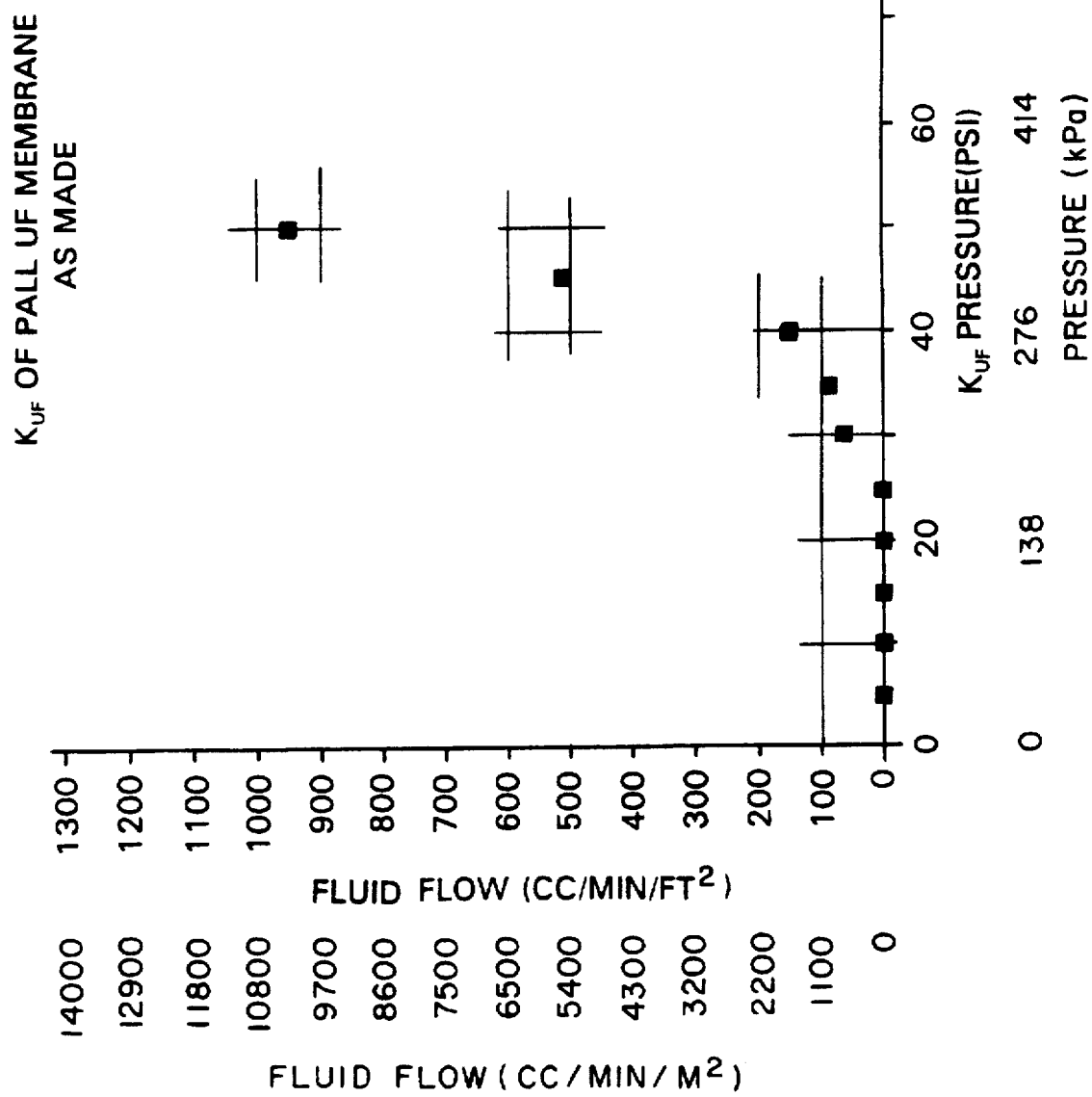
FIGS. 10A and 10B are $K_{UF}$ graphs for a membrane of the present invention comparing the $K_{UF}$ curve shape before (FIG. 10A) and after (FIG. 10B) 1 wet/dry cycle.
Figure 10B:
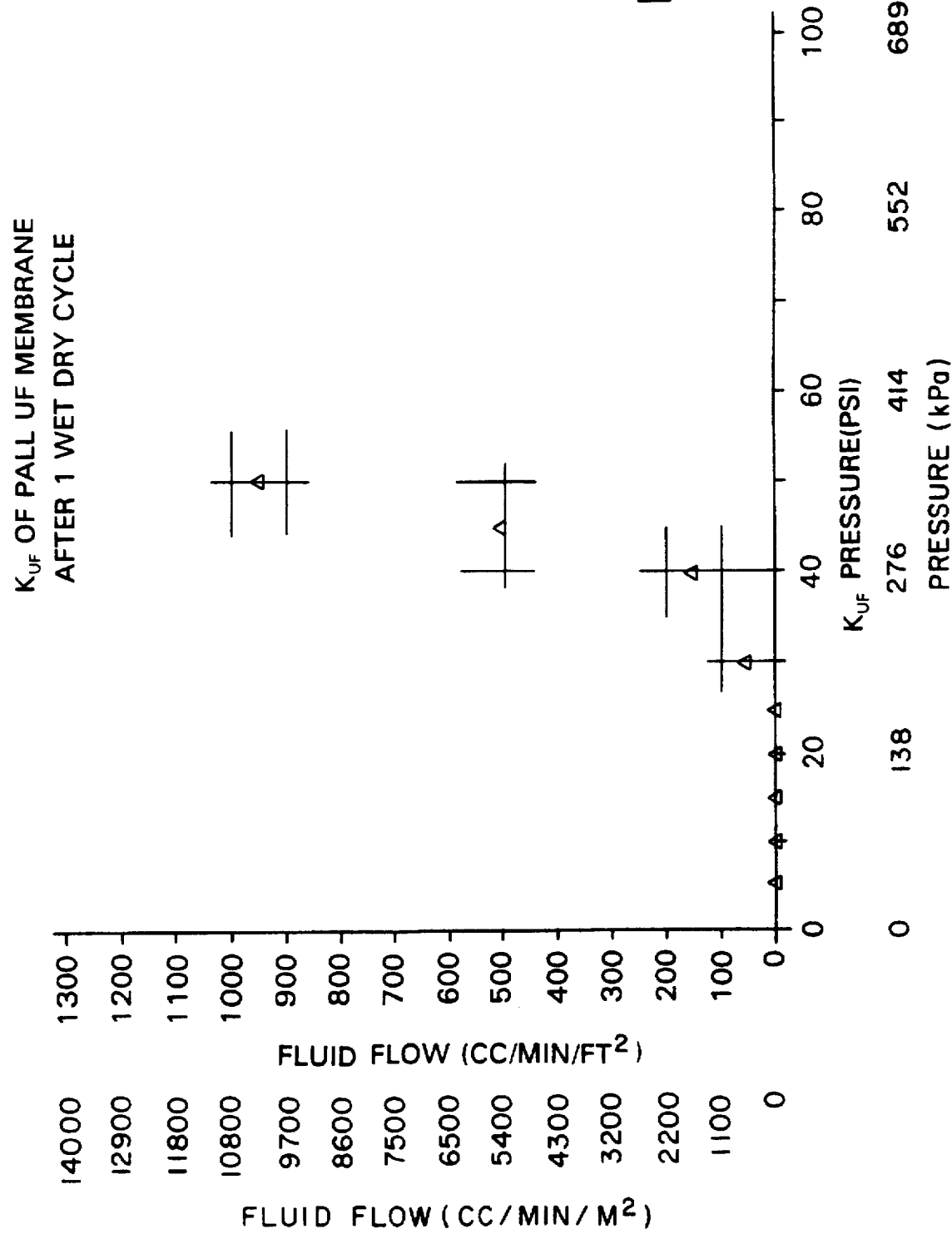

A comparison of FIGS. 10A and 10B reveals that the $K_{UF}$ curve for the membrane prepared as per the present invention was essentially unchanged after one wet/dry cycle. In the case of the Filtron Omega membrane, a comparison of FIGS. 11A and 11B reveals that after only one wet/dry cycle the shape of the curve changed. The inflection point, which determines the MWCO of the membrane, shifted to lower pressures. This indicates that after wet/dry cycling the membrane changed so as to permit larger particles to pass downstream.

Figure 11A:
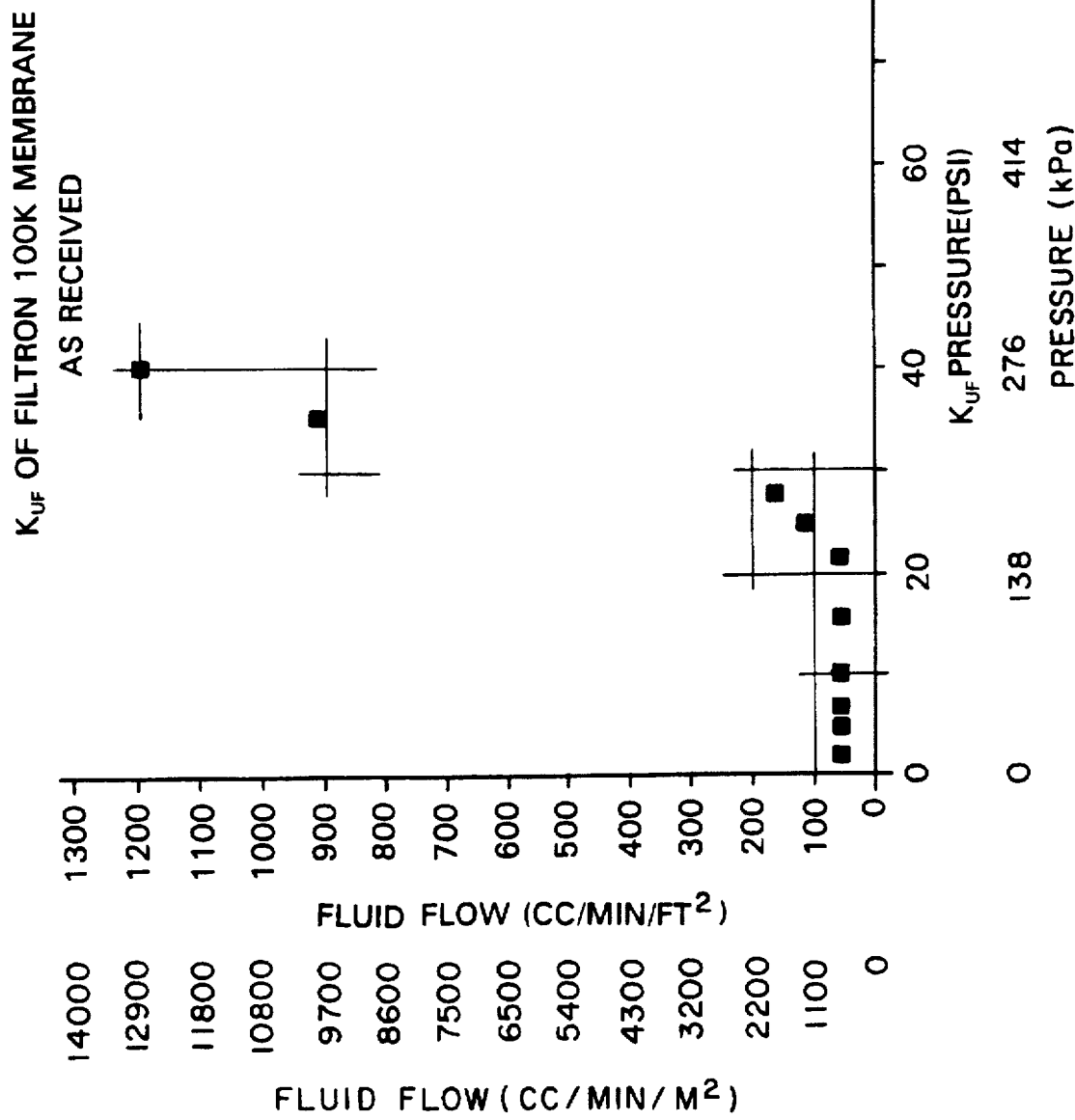
FIGS. 11A and 11B are $K_{UF}$ graphs for a commercially available UF membrane comparing the $K_{UF}$ curve shapes before (FIG. 11A) and after (FIG. 11B) 1 wet/dry cycle.
Figure 11B:
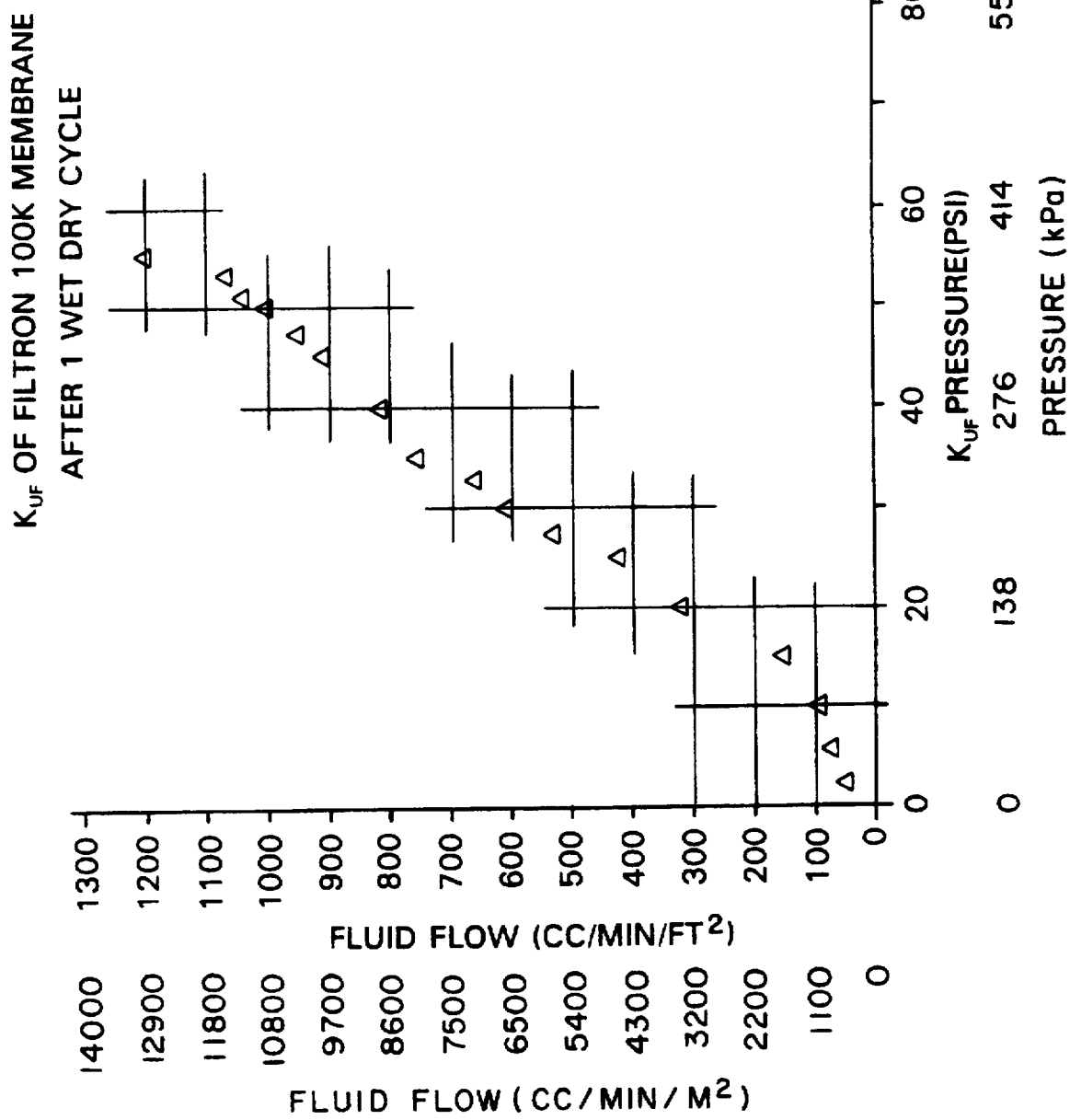

Continuing to examine the $K_{UF}$ curves of FIGS. 11A and 11B, it can be seen that, at test pressures below the inflection point there is a significant flow rate through the membrane even before wet/dry cycling. This is indicative of either defects or large pores which allow fluid flow at low test pressures.

The fact that commercially available UF membranes pass significant numbers of monodisperse latex particles much larger than the protein molecules that they are claimed to hold back is consistent with the $K_{UF}$ curves of FIGS. 11A and 11B which indicate that a significant amount of flow occurs at test pressures well below the inflection point in the $K_{UF}$ curve.

On the other hand, the membranes described in the present invention have $K_{UF}$ curves that indicate extremely low flow rates at test pressures below the inflection point. An examination of FIGS. 10A and 10B reveals that at a $K_{UF}$ test pressure of about 70 kPa (about 10 psi) the flow rate through the membrane is almost undetectable when using 1-butanol saturated with water as the wetting fluid and water saturated with 1-butanol as the displacing fluid. The 18K MWCO membranes of the present invention are also able to retain 0.02 μm latex particles as demonstrated in Table 3, indicating, that they have sharp MWCOs. In contrast, virtually all of the commercially available UF membranes failed to retain latex particles with diameters of 0.020 μm and/or 0.038 μm after they were wet/dry cycled three times and in most cases even if they were not wet/dry cycled.

EXAMPLE 16

A filtration medium in accordance with the present invention was prepared, in a manner similar to that set forth in Examples 1–9, by casting a solution of about 17 wt. % PES, 55 wt. % DMAC, and 28 wt. % PA, wherein the dissolution temperature was about 46° C. and the resin viscosity was about 650 cps. The coagulating bath was about 65 wt. % water, 23 wt. % DMAC, and 12 wt. % PA. The resin solution was cast onto a polyester fibrous nonwoven web. The resin solution flowed through the fibrous nonwoven web such that the web was embedded within the resulting membrane.

After the membrane was formed, it was surface modified by exposure to 2 Mrads E-beam radiation (with less than 50 ppm oxygen present) and then contacted with a grafting solution comprising about 2.5 vol. % HPA and 0.5 vol. % PEG 600 DM, with the remainder being a 75:25 volume ratio of water and t-butyl alcohol. The resulting filtration medium was then washed with deionized water. The CWST of the filtration medium was determined to be about 72 mN/m (about 72 dynes/cm).

EXAMPLE 17

Samples of the present inventive filtration medium of Example 16 were evaluated for titer reduction with respect to viral materials and compared with commercially available UF membranes, specifically Filtron Omega and Amicon YM100 membranes which have rated MWCO's of 100,000 daltons.

The samples of the present inventive filtration medium (dual layer) and samples of the Filtron Omega membrane (single layer and dual layer) and Amicon YM100 membrane (dual layer) were thoroughly flushed with deionized water and then subjected to a solution comprising $10^6$ PP7 bacteriophage/ml and $10^6$ PR772 coliphage/ml, as well as 5 mg/ml BSA to more closely simulate actual end-use conditions. The phage/BSA solution was forced through 47 mm diameter discs of the present inventive filtration medium and the Filtron Omega and Amicon YM100 membranes at about 105 kPa (about 15 psi) such that two 6 ml aliquots of filtrate was recovered for each filter disc sample. 5 ml of each of the two aliquots was tested for titer analysis, while the remaining 1 ml of each aliquot was subjected to a protein recovery analysis. A full titer reduction analysis was performed for the PP7 bacteriophage, while a counts/ml was determined for the PR772 coliphage. The evaluations were repeated on each of the filter disc samples. The resulting data is set forth in Table 5.

TABLE 5

| Sample | Layers | PP7 (Titer Reduction) | | PR772 (Recovery Counts/ml) | |
|---|---|---|---|---|---|
| | | Aliquot #1 | Aliquot #2 | Aliquot #1 | Aliquot #2 |
| Filtration Medium of Ex. 16 (Sample #1) | dual | $1.2 \times 10^4$ $1.6 \times 10^3$ | $1.0 \times 10^3$ $2.4 \times 10^2$ | 0 0 | 1 1.5 |
| Filtration Medium of Ex. 16 (Sample #2) | dual | $1.7 \times 10^4$ $1.0 \times 10^4$ | $3.8 \times 10^4$ $1.5 \times 10^4$ | 0.5 0.5 | 0.5 0 |
| Filtron Omega Membrane | single | $4.4 \times 10^2$ $1.9 \times 10^2$ | $1.9 \times 10^2$ $1.3 \times 10^2$ | >200 >200 | >200 >200 |
| Filtron Omega Membrane | dual | $1.8 \times 10^4$ $1.4 \times 10^3$ | $4.9 \times 10^3$ $6.7 \times 10^2$ | 73 >200 | 200 >200 |
| Amicon YM100 Membrane | dual | $1.0 \times 10^6$ $1.0 \times 10^6$ | $1.0 \times 10^6$ $1.0 \times 10^6$ | 0 0 | 0 0 |

The removal efficiency data set forth in Table 5 demonstrates the excellent removal efficiency of the present inventive filtration medium. Moreover, since the present inventive filtration medium was fully dried prior to being surface modified, i.e., radiation grafted, the data set forth in Table 5 is even more remarkable. The Filtron Omega and Amicon YM100 membranes are commercially available membranes which are supplied in a prewetted condition, and, when those membranes were dried, their structural integrities were significantly compromised, rendering those membranes useless. For example, when the glycerin present therein was removed so as to fully dry the membrane, the Amicon YM100 membrane flaked apart.

EXAMPLE 18

The present inventive filtration medium was tested for protein transmission and compared with commercially available UF membranes, specifically Filtron Omega, Filtron Nova, and Amicon YM100 membranes which have rated MWCO's of 100,000 daltons.

In particular, 47 mm discs of the present inventive filtration medium (Example 16, samples #1 and #2, dual layers), the Filtron Omega membrane (Example 17, single layer), the Filtron Nova membrane (single layer), and the Amicon YM100 membrane (single and dual layers) were subjected to water at about 105 kPa (about 15 psi) to determine water flow rate and then were subjected to a 5 mg/ml BSA solution and a 0.5 mg/ml IgG solution to determine % protein transmission. The resulting data are set forth in Table 6.

prising $3.2\times10^6$ PP7 bacteriophage/ml, $4.2\times10^6$ PR772 coliphage/ml, and 5 mg/ml BSA (to evaluate viral titer reduction), and (b) a 5 mg/ml BSA solution (to evaluate protein transmission).

The present inventive filtration medium (samples #1 and #2, both runs for each sample) exhibited absolute titer reduction with respect to PR772 coliphage (i.e., $>3.2\times10^6$ such that no PR772 coliphage was recovered in the filtrate). The observed titer reductions with respect to PP7 bacte-

TABLE 6

| | | | 5 mg/ml BSA Solution | | | 0.5 mg/ml IgG Solution | | |
|---|---|---|---|---|---|---|---|---|
| Sample | Layers | Water Flow (ml/min) | Time (min) | Volume (ml) | Protein Trans. (%) | Time (min) | Volume (ml) | Protein Trans. (%) |
| Filtration Medium of Ex. 16 (Sample #1) | dual | 3.6 | 135 | 70.5 | 92 | 180 | 40.1 | 42 |
| Filtration Medium of Ex. 16 (Sample #2) | dual | 0.8 | 120 | 52.0 | 95 | 180 | 40.9 | 64 |
| Filtron Omega Membrane | single | 41.0 | 120 | 42.9 | 86 | 195 | 38.5 | 24 |
| Filtron Nova Membrane | single | 36.0 | 120 | 38.7 | 83 | 195 | 37.6 | 23 |
| Amicon YM100 Membrane | single | 12.0 | 140 | 68.7 | 96 | 140 | 26.6 | 11 |
| Amicon YM100 Membrane | dual | 7.1 | 140 | 45.5 | 83 | 140 | 26.9 | 15 |

As demonstrated by the data set forth in Table 6, the present inventive filtration media had low water flow rates as compared to the commercially available membranes which were tested, yet the present inventive filtration media exhibited superior protein transmission.

EXAMPLE 19

A filtration medium in accordance with the present invention was prepared in a manner similar to that set forth in Example 16 except that the polyethersulfone resin was Sumikaexel® available from Sumitomo Corporation, and the grafting solution comprised about 1.5 vol. % HPA and 0.5 vol. % PEG 600 DM, with the remainder being a 75:25 volume ratio of water and t-butyl alcohol. The resulting filtration medium was then washed with deionized water.

The filtration medium was evaluated both before and after grafting. Before grafting, the filtration medium was determined to have a water flow rate at about 210 kPa (about 30 psi) of about 26 l/min/m² (about 2.4 l/min/ft²). After grafting, the filtration medium was determined to have a water flow rate at about 210 kPa (about 30 psi) of about 14 l/min/m² (about 1.3 l/min/ft²), representing a water flow rate loss of about 46%. The CWST of the grafted filtration medium was determined to be about 74–78 mN/m (about 74–78 dynes/cm).

The grafted filtration medium was then evaluated as to viral titer reduction in a manner similar to that set out in Example 17 and as to protein transmission in a manner similar to that set out in Example 18. In particular, two 47 mm diameter disc samples of the present inventive filtration medium (dual layer) were subjected to (a) a solution comriophage were quite high, albeit also somewhat mixed: absolute (i.e., $>4.2\times10^6$ such that no PP7 bacteriophage was recovered in the filtrate) (samples #1 and #2, first runs each), $1.7\times10^5$ (sample #1, second run), and $4.9\times10^5$ (sample #2, second run). The present inventive filtration medium exhibited a 91% protein transmission of the 5 mg/ml BSA solution (180 minutes filtration time; 75.8 ml total volume).

EXAMPLE 20

Filtration media in accordance with the present invention were prepared in a manner similar to that set forth in Example 16 except that the polyethersulfone resin was Sumikaexel® available from Sumitomo Corporation, and the grafting solution comprised about 1.5 vol. % HPA and 0.5 vol. % PEG 600 DM, with the remainder being a 75:25 volume ratio of water and t-butyl alcohol. The resulting filtration media were then washed with deionized water.

The filtration media were evaluated in terms of water flow rate at about 210 kPa (about 30 psi), viral titer reduction in a manner similar to that set out in Example 17 except using 47 mm diameter discs of the filtration media at an applied pressure of about 21 kPa (about 3 psi), and protein transmission in a manner similar to that set out in Example 18 except using 142 mm diameter discs of the filtration media at an applied pressure of about 21 kPa (about 3 psi). In particular, the present inventive filtration media (dual layer) were subjected to solutions comprising $10^6$ PP7 bacteriophage/ml and $10^6$ PR772 coliphage/ml, 5 mg/ml BSA, and 0.5 mg/ml IgG. The resulting data are set forth in Tables 7 and 8.

TABLE 7

| Sample | Layers | PP7 (Titer Reduction) Aliquot #1 | PP7 (Titer Reduction) Aliquot #2 | PR772 (Titer Reduction) Aliquot #1 | PR772 (Titer Reduction) Aliquot #2 |
|---|---|---|---|---|---|
| 20A | dual | $8.0 \times 10^5$ | $8.0 \times 10^5$ | $>1.8 \times 10^6$ | $>1.8 \times 10^6$ |
|  |  | $1.0 \times 10^5$ | $1.0 \times 10^5$ | $>1.8 \times 10^6$ | $>1.8 \times 10^6$ |
| 20B | dual | $6.2 \times 10^4$ | $6.6 \times 10^4$ | — | — |
|  |  | $1.2 \times 10^4$ | $1.1 \times 10^4$ | — | — |

TABLE 8

| Sample | Layers | Water Flow (ml/min/m$^2$) | 5 mg/ml BSA Solution Time (min) | 5 mg/ml BSA Solution Volume (ml) | 5 mg/ml BSA Solution Protein Trans. (%) | 0.5 mg/ml IgG Solution Time (min) | 0.5 mg/ml IgG Solution Volume (ml) | 0.5 mg/ml IgG Solution Protein Trans. (%) |
|---|---|---|---|---|---|---|---|---|
| 20A | dual | 10.8 | 165 | 64.8 | 98 | 180 | 46.7 | 69 |
| 20B | dual | 11.8 | 165 | 44.0 | 94 | 180 | 67.7 | 84 |
| 20C | dual | 15.1 | 139 | 80.6 | 99 | — | — | — |
| 20D | dual | 16.7 | 139 | 75.7 | 99 | — | — | — |
| 20E | dual | 10.8 | 139 | 85.0 | 99 | — | — | — |
| 20F | dual | 12.9 | 155 | 92.2 | 100 | — | — | — |
| 20G | dual | 14.0 | 155 | 97.0 | 100 | — | — | — |
| 20H | dual | 16.1 | 155 | 84.5 | 100 | — | — | — |

As demonstrated by the data set forth in Tables 7 and 8, the present inventive filtration media exhibit excellent viral titer reductions and protein transmission, even at relatively low applied pressures.

All of the references cited herein are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A filtration medium comprising (a) a skinned ultrafiltration membrane and a monomer surface coating thereon of an acrylic or methacrylic acid monomer having alcohol functional groups and (b) a fibrous nonwoven web embedded in said membrane, wherein said filtration medium after having been fully dried is characterized by having a titer reduction of at least about $10^3$ with respect to PP7 bacteriophage and a critical wetting surface tension of at least about 70 mN/m.

2. The filtration medium of claim 1, wherein said filtration medium after having been fully dried is characterized by having a titer reduction of at least about $10^3$ with respect to PP7 bacteriophage in the presence of 5 mg/ml BSA.

3. A method of filtering a fluid comprising passing a fluid through the filtration medium of claim 2.

4. The filtration medium of claim 1, wherein said membrane is comprised of a polysulfone.

5. The filtration medium of claim 4, wherein said polysulfone is a polyethersulfone.

6. A method of filtering a fluid comprising passing a fluid through the filtration medium of claim 5.

7. The filtration medium of claim 3, wherein said polysulfone is a polyphenylsulfone.

8. The filtration medium of claim 1, wherein said acrylic or methacrylic monomer is selected from the group consisting of hydroxyethylacrylate, hydroxyethylmethacrylate, hydroxypropylacrylate, hydroxypropylmethacrylate, and combinations thereof.

9. The filtration medium of claim 8, wherein said acrylic or methacrylic monomer is selected from the group consisting of hydroxypropylacrylate and hydroxyethylmethacrylate.

10. A method of filtering a fluid comprising passing a fluid through the filtration medium of claim 8.

11. The filtration medium of claim 1, wherein said filtration medium after having been fully dried has a titer reduction of at least about $10^5$ with respect to PP7 bacteriophage.

12. The filtration medium of claim 11, wherein said filtration medium after having been fully dried is characterized by having a titer reduction of at least about $10^5$ with respect to PP7 bacteriophage in the presence of 5 mg/ml BSA.

13. The filtration medium of claim 11, wherein said filtration medium after having been fully dried has a titer reduction of at least about $10^6$ with respect to PP7 bacteriophage.

14. A method of filtering a fluid comprising passing a fluid through the filtration medium of claim 13.

15. The filtration medium of claim 1, wherein said filtration medium after having been fully dried has a critical wetting surface tension of at least about 72 mN/m.

16. The filtration medium of claim 15 wherein said filtration medium after having been fully dried has a critical wetting surface tension of at least about 74 mN/m.

17. A method of filtering a fluid comprising passing a fluid through the filtration medium of claim 15.

18. The filtration medium of claim 1, wherein said membrane is comprised of a polyethersulfone, said acrylic or methacrylic monomer is selected from the group consisting of hydroxypropylacrylate and hydroxyethylmethacrylate, and said filtration medium after having been fully dried is characterized by having a titer reduction of at least about $10^6$ with respect to PP7 bacteriophage and a critical wetting surface tension of at least about 74 mN/m.

19. A method of filtering a fluid comprising passing a fluid through the filtration medium of claim 18.

20. The filtration medium of claim 1, wherein said filtration medium after having been fully dried is characterized by a BSA protein transmission of at least about 85% as tested using a 47 mm diameter disc to filter 50 ml of a 5 mg/ml BSA solution at about 21 kPa applied pressure.

21. The filtration medium of claim 20, wherein said membrane is comprised of a polyethersulfone, said acrylic or methacrylic monomer is selected from the group consisting of hydroxypropylacrylate and hydroxyethylmethacrylate, and said filtration medium after having been fully dried is characterized by having a titer reduction of at least about $10^6$ with respect to PP7 bacteriophage, a critical wetting surface tension of at least about 74 mN/m, and a BSA protein transmission of at least about 95%.

22. A method of filtering a fluid comprising passing a fluid through the filtration medium of claim 21.

23. The filtration medium of claim 20, wherein said filtration medium after having been fully dried is characterized by a IgG protein transmission of at least about 40% as tested using a 47 mm diameter disc to filter 40 ml of a 0.5 mg/ml IgG solution at about 21 kPa applied pressure.

24. The filtration medium of claim 23, wherein said membrane is comprised of a polyethersulfone, said acrylic or methacrylic monomer is selected from the group consisting of hydroxypropylacrylate and hydroxyethylmethacrylate, and said filtration medium after having been fully dried is characterized by having a titer reduction of at least about $10^6$ with respect to PP7 bacteriophage, a critical wetting surface tension of at least about 74 mN/m, and an IgG protein transmission of at least about 60%.

25. A method of filtering a fluid comprising passing a fluid through the filtration medium of claim 24.

26. A method of filtering a fluid comprising passing a fluid through the filtration medium of claim 23.

27. A method of filtering a fluid comprising passing a fluid through the filtration medium of claim 20.

28. A method of filtering a fluid comprising passing a fluid through the filtration medium of claim 1.

29. A method of preparing a filtration medium comprising (a) dissolving a polymeric resin in a carrier comprising both a solvent for the resin and a nonsolvent for the resin to thereby form a solution, wherein the resin is present in an amount from about 15–20 wt. % of the solution, and the amount of nonsolvent is from about 26–34 wt. % of the solution, with the ratio of solvent to nonsolvent being from about 1.5:1 to about 2:1, (b) rapidly mixing the solution to reduce or eliminate the presence of gel particles, (c) filtering the solution to remove any gel particles that are present therein, (d) degassing the solution to remove any entrained gas, (e) casting or spinning the solution onto a fibrous nonwoven support so as to envelope said fibrous nonwoven support, (f) contacting the resulting cast or spun solution with a setting bath that comprises both a solvent and a nonsolvent for the resin to form a skinned ultrafiltration membrane, and (g) grafting the resulting membrane with a monomer of an acrylic or methacrylic acid monomer having alcohol functional groups such that the monomer coats the surface of the membrane so as to form a filtration medium after having been fully dried characterized by having a titer reduction of at least about $10^3$ with respect to PP7 bacteriophage and a critical wetting surface tension of at least about 70 mN/m.

30. The method of claim 29, wherein said filtration medium after having been fully dried is characterized by having a titer reduction of at least about $10^3$ with respect to PP7 bacteriophage in the presence of 5 mg/ml BSA.

31. The method of claim 29, wherein said polymeric resin is a polysulfone.

32. The method of claim 31, wherein said polysulfone is a polyethersulfone.

33. The method of claim 31, wherein said polysulfone is a polyphenylsulfone.

34. The method of claim 29, wherein said acrylic or methacrylic monomer is selected from the group consisting of hydroxyethylacrylate, hydroxyethylmethacrylate, hydroxypropylacrylate, hydroxypropylmethacrylate, and combinations thereof.

35. The method of claim 34, wherein said acrylic or methacrylic monomer is selected from the group consisting of hydroxypropylacrylate and hydroxyethylmethacrylate.

36. The method of claim 29, wherein said filtration medium after having been fully dried has a titer reduction of at least about $10^5$ with respect to PP7 bacteriophage.

37. The method of claim 36, wherein said filtration medium after having been fully dried has a titer reduction of at least about $10^6$ with respect to PP7 bacteriophage.

38. The method of claim 29, wherein said filtration medium after having been fully dried has a critical wetting surface tension of at least about 72 mN/m.

39. The method of claim 38, wherein said filtration medium after having been fully dried has a critical wetting surface tension of at least about 74 mN/m.

40. The method of claim 29, wherein said polymer resin is a polyethersulfone, said acrylic or methacrylic monomer is selected from the group consisting of hydroxypropylacrylate and hydroxyethylmethacrylate, and said filtration medium after having been fully dried is characterized by having a titer reduction of at least about $10^6$ with respect to PP7 bacteriophage and a critical wetting surface tension of at least about 74 mN/m.

41. The method of claim 29, wherein said filtration medium after having been fully dried is characterized by a BSA protein transmission of at least about 85% as tested using a 47 mm diameter disc to filter 50 ml of a 5 mg/ml BSA solution at about 21 kPa applied pressure.

42. The method of claim 41, wherein said polymer resin is a polyethersulfone, said acrylic or methacrylic monomer is selected from the group consisting of hydroxypropylacrylate and hydroxyethylmethacrylate, and said filtration medium after having been fully dried is characterized by having a titer reduction of at least about $10^6$ with respect to PP7 bacteriophage, a critical wetting surface tension of at least about 74 mN/m, and a BSA protein transmission of at least about 95%.

43. The method of claim 41, wherein said filtration medium after having been fully dried is characterized by a IgG protein transmission of at least about 40% as tested using a 47 mm diameter disc to filter 40 ml of a 0.5 mg/ml IgG solution at about 21 kPa applied pressure.

44. The method of claim 43, wherein said polymer resin is a polyethersulfone, said acrylic or methacrylic monomer is selected from the group consisting of hydroxypropylacrylate and hydroxyethylmethacrylate, and said filtration medium after having been fully dried is characterized by having a titer reduction of at least about $10^6$ with respect to PP7 bacteriophage, a critical wetting surface tension of at least about 74 mN/m, and an IgG protein transmission of at least about 60%.

* * * * *